(12) United States Patent
Stoeber et al.

(10) Patent No.: US 10,458,892 B2
(45) Date of Patent: Oct. 29, 2019

(54) MICROFLUIDIC-BASED REAL-TIME DETECTOR FOR FINE PARTICULATE MATTER

(71) Applicant: THE UNIVERSITY OF BRITISH COLUMBIA, Vancouver (CA)

(72) Inventors: Boris Stoeber, Vancouver (CA); Winnie Chu, Lions Bay (CA); Leon Yuen, Richmond (CA)

(73) Assignee: The University of British Columbia, Vancouver (CA)

(*) Notice: Subject to any disclaimer, the term of this patent is extended or adjusted under 35 U.S.C. 154(b) by 61 days.

(21) Appl. No.: 15/523,656

(22) PCT Filed: Oct. 26, 2015

(86) PCT No.: PCT/CA2015/051086
§ 371 (c)(1),
(2) Date: May 1, 2017

(87) PCT Pub. No.: WO2016/065465
PCT Pub. Date: May 6, 2016

(65) Prior Publication Data
US 2017/0336312 A1 Nov. 23, 2017

Related U.S. Application Data

(60) Provisional application No. 62/073,811, filed on Oct. 31, 2014.

(51) Int. Cl.
*G01N 15/06* (2006.01)
*G01N 15/14* (2006.01)

(52) U.S. Cl.
CPC ......... *G01N 15/06* (2013.01); *G01N 15/1459* (2013.01); *G01N 15/1484* (2013.01);
(Continued)

(58) Field of Classification Search
CPC .............. G01N 15/06; G01N 15/1459; G01N 15/1484; G01N 2015/0693;
(Continued)

(56) References Cited

U.S. PATENT DOCUMENTS

| 5,553,795 A | 9/1996 | Tsai et al. |
| 6,284,025 B1 | 9/2001 | Kreisberg et al. |

(Continued)

FOREIGN PATENT DOCUMENTS

| WO | 2012055048 A1 | 5/2012 |
| WO | 2013017832 A1 | 2/2013 |

OTHER PUBLICATIONS

Yuen, L. et al., "Microfluidic-Based Real-Time Detector for Fine Particulate Matter", IEEE Sensors Journal, Nov. 2-5, 2014, pp. 775-778.

(Continued)

*Primary Examiner* — John H Le
(74) *Attorney, Agent, or Firm* — Oyen Wiggs Green & Mutala LLP

(57) ABSTRACT

An apparatus for monitoring particulate matter includes a fluid flow passage. Some embodiments include a cartridge defining a part of the fluid flow passage extending from a cartridge inlet to a cartridge outlet and a particle size selector in the fluid-flow passage between the cartridge inlet and the cartridge outlet. The particle size selector comprises a curve section in the fluid flow passage where the flow of fluid undergoes a change in direction and an impact surface extending transversely to the fluid flow passage on an outside of the curve. A particle counter is located downstream from the particle size selector. A pump is connected to drive a flow of a fluid containing the particulate matter through the fluid flow passage. The apparatus may be made compact. Embodiments may be worn and used to monitor exposure of persons to particulate matter. Example embodiments may be worn as portable personal devices, fixed in place to monitor particulate matter in specific areas, integrated into heating ventilating and air conditioning (HVAC) apparatus or provided in hand-held devices for spot-testing.

20 Claims, 26 Drawing Sheets

(52) U.S. Cl.
CPC ............... *G01N 2015/0693* (2013.01); *G01N 2015/149* (2013.01); *G01N 2015/1486* (2013.01); *G01N 2015/1493* (2013.01)

(58) Field of Classification Search
CPC ..... G01N 2015/1486; G01N 2015/149; G01N 2015/1493
USPC .................. 702/26, 45; 435/7.1; 73/28.04
See application file for complete search history.

(56) References Cited

U.S. PATENT DOCUMENTS

| | | |
|---|---|---|
| 6,386,015 B1 | 5/2002 | Rader et al. |
| 7,604,676 B2 | 10/2009 | Braziunas |
| 7,799,567 B1 | 9/2010 | Call |
| 8,009,290 B2 | 8/2011 | Unger |
| 9,141,094 B2 | 9/2015 | Pariseau et al. |
| 9,541,475 B2 * | 1/2017 | Chu .................. G01N 15/0255 |
| 2007/0178529 A1 * | 8/2007 | Breidford ............... B01F 11/04 435/7.1 |
| 2013/0213115 A1 | 8/2013 | Chu et al. |
| 2014/0277624 A1 | 9/2014 | Pariseau et al. |
| 2014/0281659 A1 | 9/2014 | Pariseau |

OTHER PUBLICATIONS

Zhang, J. et al., "Inertial particle separation by differential equilibrium positions in a symmetrical serpentine micro-channel", Scientific Reports, vol. 4, Mar. 31, 2014, Article No. 4527.

Schaap, A. et al., "Transport of airborne particles in straight and curved microchannels", Physics of Fluids, vol. 24, Issue 8, 2012, p. 083301.

Schaap, A. et al., "Continuous size-separation of airborne particles in a microchannel for aerosol monitoring", IEEE Sensors Journal, vol. 11, issue 11, p. 2790-2797, 2011.

* cited by examiner

MICROFLUIDIC-BASED REAL-TIME DETECTOR FOR FINE PARTICULATE MATTER

CROSS-REFERENCE TO RELATED APPLICATIONS

This application claims priority from U.S. Application No. 62/073,811 filed 31 Oct. 2014. For purposes of the United States, this application claims the benefit under 35 U.S.C. § 119 of U.S. Application No. 62/073,811 filed 31 Oct. 2014 and entitled MICROFLUIDIC-BASED REAL-TIME DETECTOR FOR FINE PARTICULATE MATTER which is hereby incorporated herein by reference for all purposes.

FIELD OF THE INVENTION

This invention relates to apparatus and methods for monitoring particulate matter in fluids. Some embodiments provide methods and apparatus for monitoring for particles in certain size ranges in air.

BACKGROUND

Long- and short-term exposure to particulate matter smaller than 2.5 µm diameter (PM 2.5) is linked to a wide range of harmful cardiovascular and respiratory health effects [1]. The US Environmental Protection Agency revised the annual average PM 2.5 concentration limit in 2013 from 15 to 12 µg/m$^3$ and estimated that meeting the new standard will result in $4 to $9 billion in annual health benefits [2]. The concentration level of PM 2.5 is currently monitored by sparsely distributed monitoring stations set up by environment agencies to assess air quality in different regions.

There is a need for cost effective ways to monitor local personal exposure to particulate matter in air especially in densely populated cities and hazardous occupational environments (where the concentration level frequently exceeds the recommended limits). There is a particular need for such ways which are capable of real-time monitoring (e.g. capable of completing a measure of a level of particulates in a few minutes—such as less than 15 minutes or less than 7 minutes). Advantageously such ways would be capable of determining particle concentrations according to accepted standards such as PM2.5.

SUMMARY

This invention has a number of aspects. These aspects provide methods and apparatus for monitoring particulate matter, for example to determine the concentration of particulate matter in a fluid. For example, the apparatus may count the number and/or volume and/or mass of particles in one or more defined size ranges per unit volume of a fluid such as air. Particulate matter may comprise solid particles or liquid particles. For example, tiny liquid droplets (e.g. aerosols) are a type of particulate matter. Some embodiments provide personal monitors that may be worn by a person or situated in a person's workplace to monitor exposure of the person to airborne particulate matter. Some embodiments provide particulate monitors that may be distributed at various locations to monitor environmental levels of particulate matter.

One aspect provides an apparatus for monitoring particulate matter. In some embodiments elements operative to perform size selection of particles (for example, by removing particles larger than a certain size) are provided in a replaceable cartridge. Such apparatus for example, may be carried (e.g. worn) by a person to monitor that person's personal exposure to particulates or used to monitor the concentration of particulates at certain locations. The cartridge may be replaced.

In an example embodiment the apparatus defines a fluid flow passage and comprises a cartridge defining a part of the fluid flow passage extending from a cartridge inlet to a cartridge outlet. A particle size selector is provided in the fluid-flow passage between the cartridge inlet and the cartridge outlet. The particle size selector comprises a portion of the fluid-flow passage in which a direction of flow changes. For example, the particle size selector may comprise an inlet in which fluid flows in a first direction and an outlet in which fluid flows in a second direction that is at an angle to the first direction (e.g. 90 degrees or another suitable angle). In between the inlet and outlet of the particle size selector there is a section of the fluid-flow passage in which the direction of fluid flow changes from the inlet direction to the outlet direction. This section of the fluid-flow passage may comprise, for example, one or more of: a curved or bent section of the fluid flow passage, a chamber, or the like. An impact surface extends transversely to the fluid flow passage on an outside of the curve.

In some embodiments, the fluid flow passage is expanded in width to provide a chamber on the outside of the curve and the impact surface defines a downstream edge of the chamber. The chamber serves as a trap for particles too large to be carried around the corner by the flow. Fluid flow velocity is low in the chamber. Such a particle trapping chamber or 'trapping region' may trap particles in various ways. Some particles may be trapped when they hit the impact surface. Other particles may arrive in the trapping region with relatively low velocity and may become trapped without impacting the impact surface.

A particle counter located is downstream from the particle size selector. The particle detector or parts of it may be incorporated into the cartridge in some embodiments. In other embodiments the particle detector is downstream from the cartridge outlet. A pump is connected to drive a flow of a fluid containing the particulate matter through the fluid flow passage. In some embodiments the particle size selector passes particles smaller than a given size (e.g. smaller than 2.5 µm or 3 µm) but blocks larger particles.

Another aspect provides cartridges for use in particle monitoring. The cartridges each comprise a package having a fluid flow passage extending from a cartridge inlet to a cartridge outlet. A particle size selector is provided in the fluid-flow passage between the cartridge inlet and the cartridge outlet. The particle size selector may, for example, have a construction as described above. For example, the particle size selector may comprise a portion of the fluid flow passage in which the fluid follows a curved path. An impact surface extends transversely to the curved path on an outside of the curved path.

The cartridge may optionally contain other features. For example, in some embodiments all or one or more components of a particle detector may be provided in the cartridge. In some embodiments the cartridge comprises optical windows on either side of the fluid flow path downstream from the particle size selector. An optical particle detector outside of the cartridge may detect particles in the fluid flow passage through the windows. In some embodiments one or more other optical components such as lenses are formed in the cartridge and the optical particle detector comprises a light source and light detector separate from the cartridge. In some embodiments the cartridge comprises a battery that may power various parts of a particle monitoring apparatus (e.g. a pump and/or a particle detector and/or a processor or other electronics) when the cartridge is installed in the particle monitoring apparatus.

Another aspect provides apparatus for monitoring particulate matter. The apparatus comprises a fluid flow passage having an inlet and an outlet and a particle size selector in the fluid-flow passage between the inlet and the outlet. The particle size selector comprises section of the fluid flow passage in which flowing fluid changes direction (e.g. follows a curve). The particle size selector may have a construction as described above, for example, with an impact surface that extends transversely to the fluid flow passage on an outside of the curve. An accelerating nozzle is provided immediately upstream from the curve. The width of the fluid flow passage is reduced in the accelerating nozzle. A particle counter is located downstream from the particle size selector. A pump is connected to drive a flow of a fluid containing the particulate matter through the fluid flow passage.

The invention contemplates embodiments that:
- Include or do not include removable/replaceable cartridges containing one or more particle size selectors (which may be impactor-type particle size selectors); and/or
- Include or do not include impactor type particle size selectors which include accelerating nozzle sections upstream from a location in which a particle direction changes. In the accelerating nozzle section a flow of fluid is constricted. In some embodiments this constriction causes particles entrained in the flowing fluid to become concentrated in a central portion of the flowing fluid before causing the fluid to flow around a curve; and/or
- Include or do not include impactor-type particle size selectors which include a trapping chamber adjacent to an impact surface and have one or more ports in the trapping chamber that may be operated to either or both introduce fluid into the trapping chamber or bleed fluid from the trapping chamber. Such ports may be applied, for example, for the purpose of removing trapped particles from the trapping chamber; and/or
- Include or do not include impactor-type particle size selectors which comprise flattened microfluidic fluid-flow passages formed in a body of a mouldable material; and/or
- Include or do not include two or more impactor-type particle size selectors connected in a series or cascade fashion; and/or
- Perform particle monitoring methods as described herein using flow rates of 1 l/min or less; and/or
- Provide or do not provide particle monitoring systems designed to be portable or wearable.

Another aspect provides methods for monitoring particulate matter in a gas, for example, air. The methods comprise flowing a gas containing particulate matter through a fluid flow passage, performing a particle size selection in the fluid flow passage, and counting particles entrained in the gas downstream from the particle size selection. In some embodiments, performing particle size selection comprises flowing the gas into a chamber through an inlet portion of the fluid flow passage extending in a first direction, flowing the gas out of the chamber through an outlet portion of the fluid flow passage extending in a second direction at an angle to the first direction and allowing particles larger than a target size to be removed from the flow by interacting with an impingement surface in the chamber. The impingement surface may extend transversely to the fluid flow passage at a downstream end of the chamber. In some embodiments, the method comprises accelerating the flow in the inlet portion of the fluid flow passage.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIG. 6 is a graph comparing penetration efficiency measured for a prototype impactor to simulations.

FIG. 7 illustrates detector characterization with 1.5 μm particles for 1 minute sampling intervals for an example embodiment, error bars correspond to ±1 standard deviation.

FIG. 8 schematically illustrates force balance in an impactor-type particle size selector.

FIG. 9 illustrates a sample cut-off curve for an example embodiment.

FIG. 10 illustrates transmission ratio based on analytical expressions of particle radial displacement for outlet angles of 45, 90 and 135 degrees for an example embodiment.

FIG. 11A illustrates a flow velocity profile for an inlet having an angle of 45 degrees.

FIG. 11B illustrates flow velocity profile for an inlet having an angle of 75 degrees.

FIGS. 12A to 12D illustrate acceleration nozzle inlets having angles of 30, 45, 60, and 75 degrees according to various example embodiments.

FIG. 13A illustrates an example flow velocity profile for an impactor having no acceleration nozzle.

FIG. 13B illustrates fan example flow velocity profile for an impactor with an acceleration nozzle.

FIG. 14 illustrates example transmission curves for impactor-type particle size selectors with and without an acceleration nozzle.

FIG. 15 illustrates a geometry for an impactor-type particle size selector having nozzle length L, nozzle width W, outlet width S, and impactor width Wi according to an example embodiment.

FIG. 16A illustrates an example flow velocity profile for S=0.5 Wn according to an example embodiment. FIG. 16B illustrates an example transmission ratio curve for S=0.5 Wn for freeze, 50% freeze and bounce wall conditions.

Figure 17A:
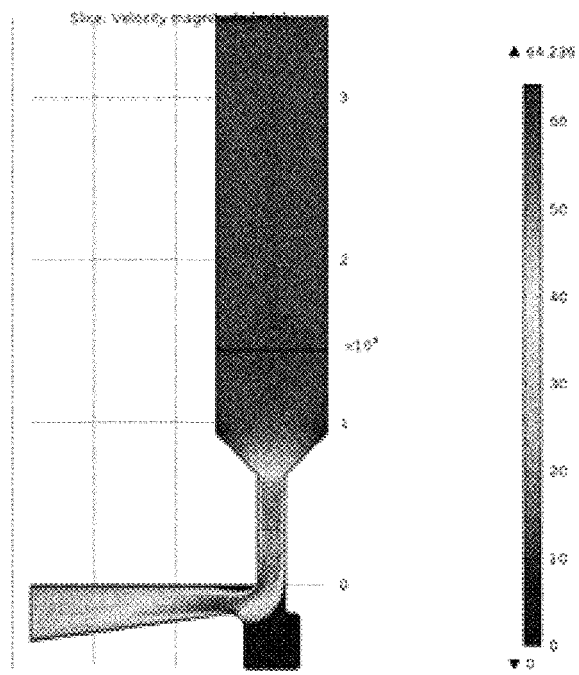
Figure 17B:
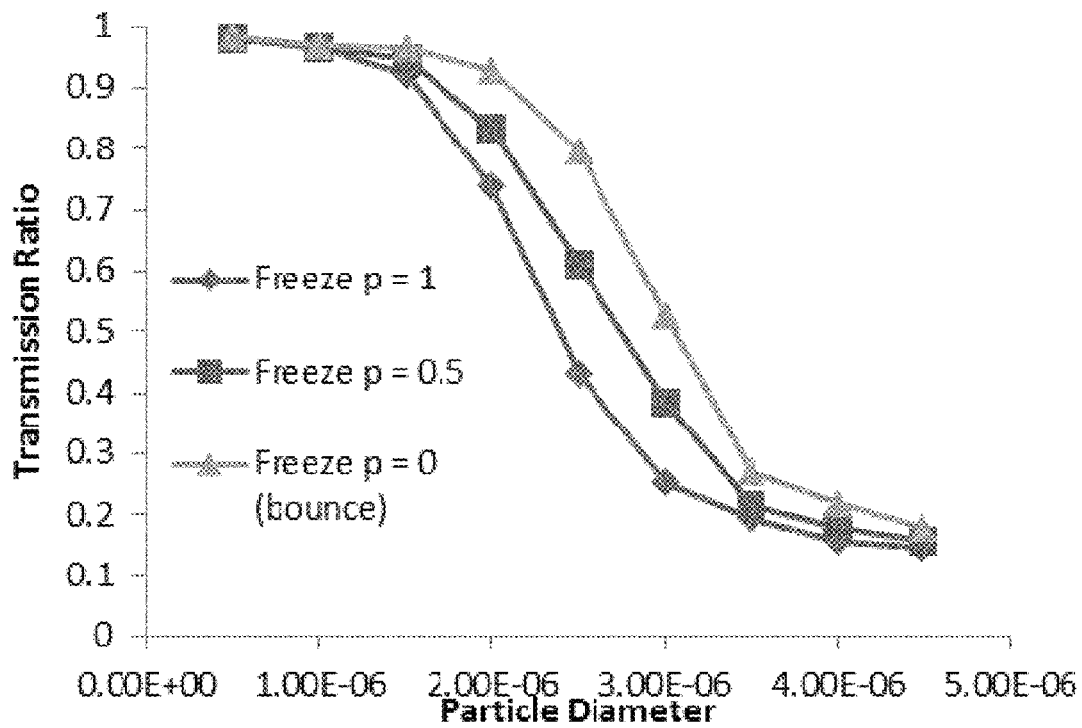

FIG. 17A illustrates an example flow velocity profile for S=Wn according to an example embodiment. FIG. 17B illustrates transmission curve ratios for S=Wn for freeze, 50% freeze and bounce wall conditions.

Figure 18A:
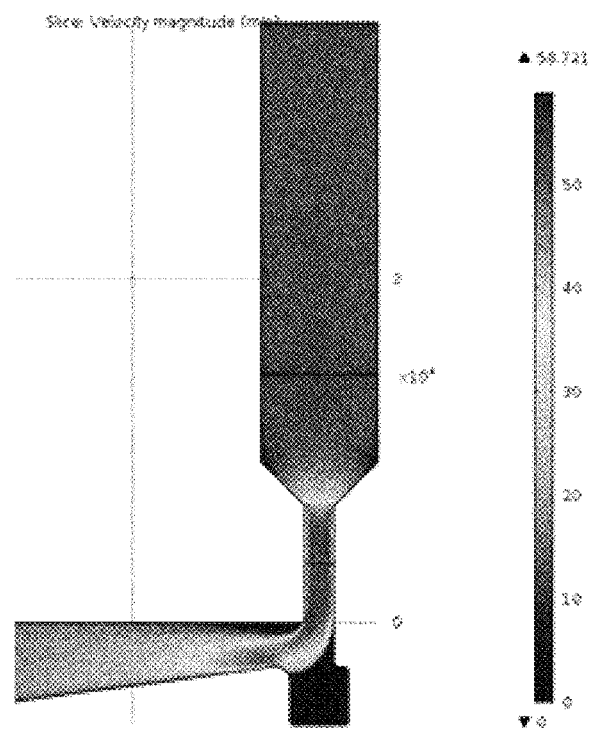
Figure 18B:
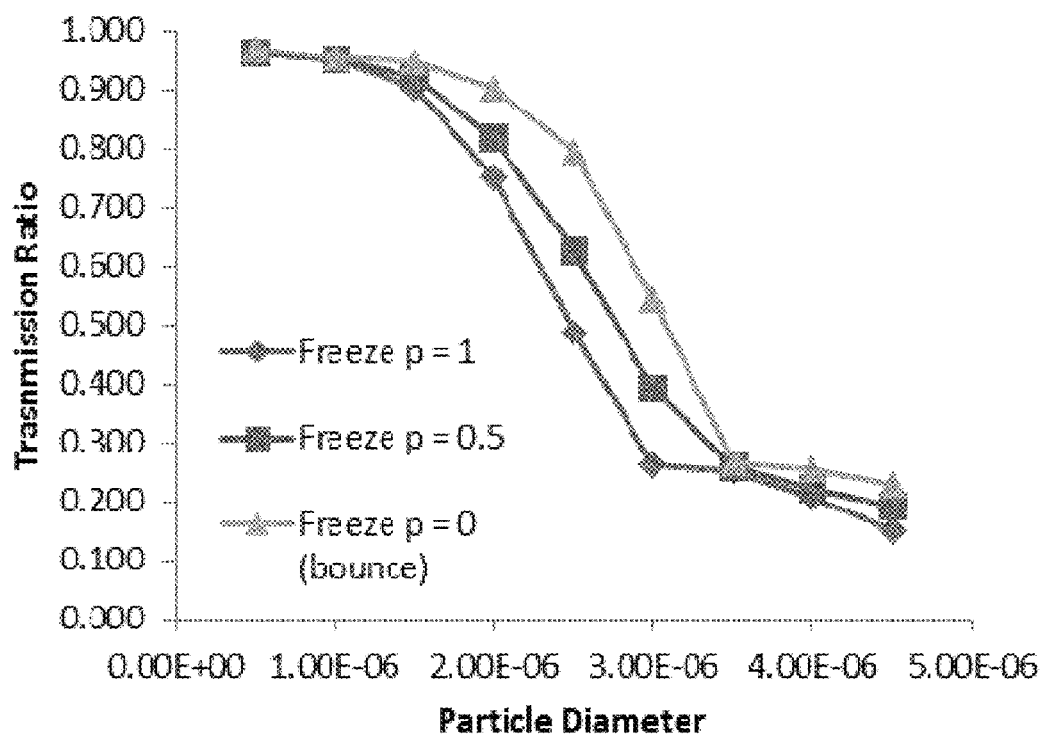

FIG. 18A illustrates flow velocity profile for S=1.5 Wn according to an example embodiment. FIG. 18B illustrates transmission curve ratios for S=1.5 Wn for freeze, 50% freeze and bounce wall conditions.

Figure 19A:
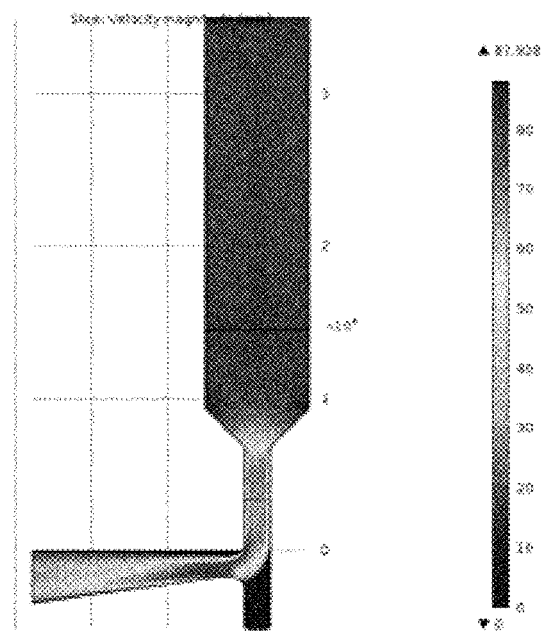
Figure 19B:
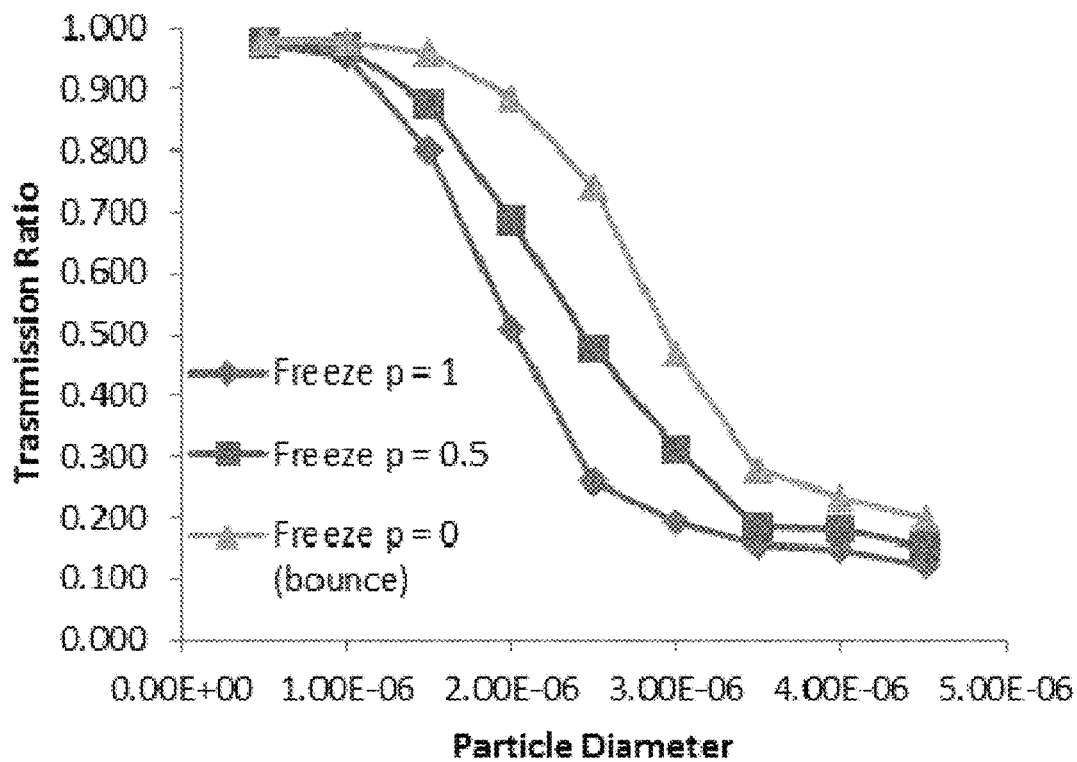

FIG. 19A illustrates flow velocity profile for Wi=0.5 Wn according to an example embodiment. FIG. 19B illustrates transmission curve ratios for Wi=0.5 Wn for freeze, 50% freeze and bounce wall conditions.

Figure 20A:
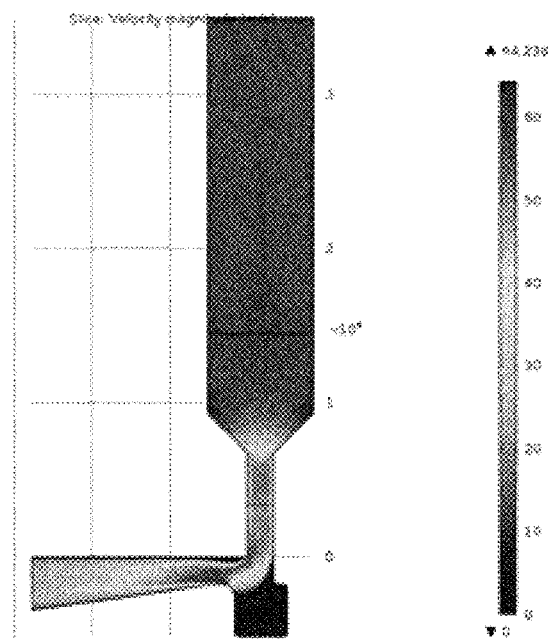
Figure 20B:
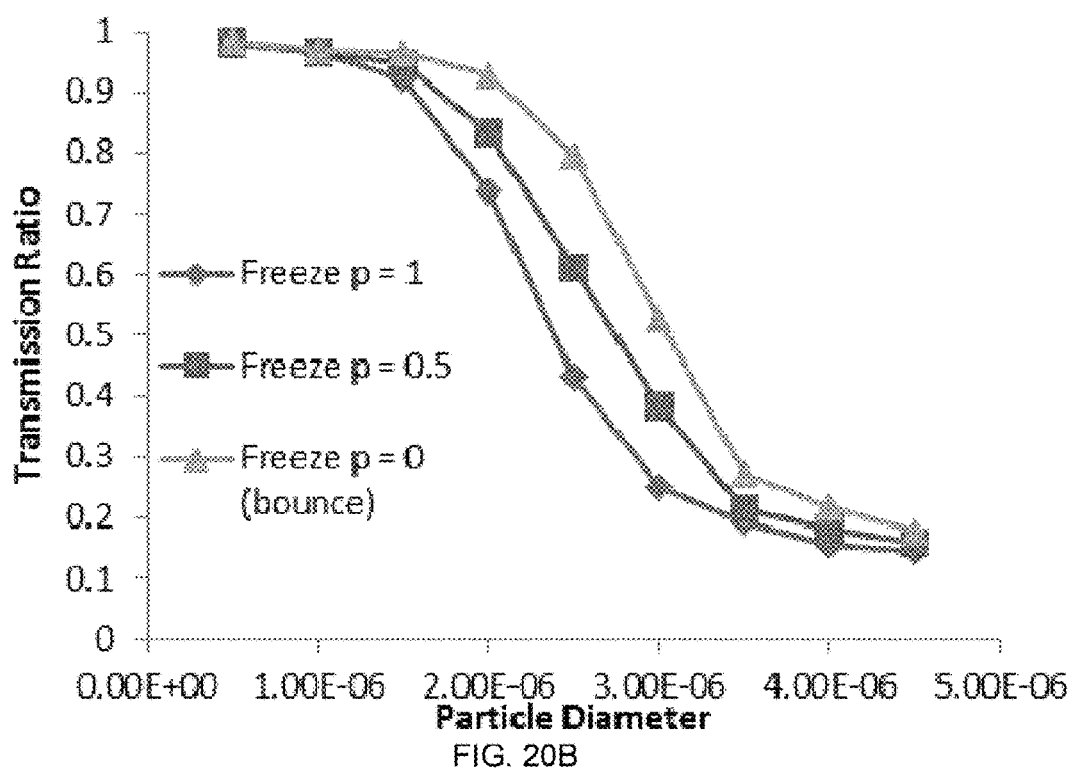

FIG. 20A illustrates flow velocity profile for Wi=Wn according to an example embodiment. FIG. 20B illustrates transmission curve ratio for Wi=Wn for freeze, 50% freeze and bounce wall condition according to an example embodiment.

Figure 21A:
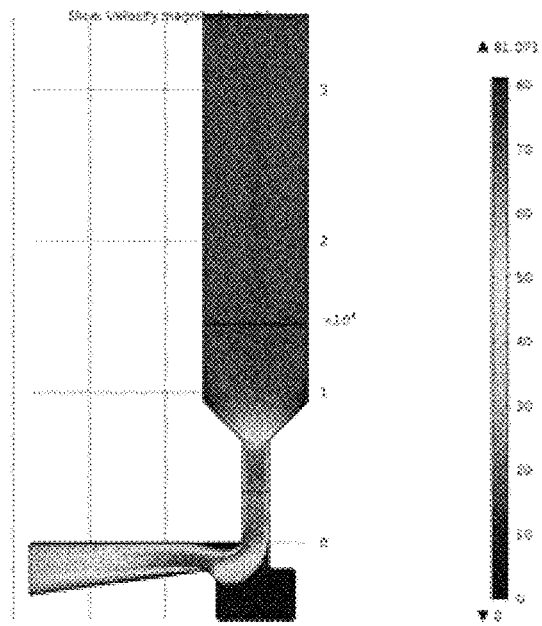
Figure 21B:
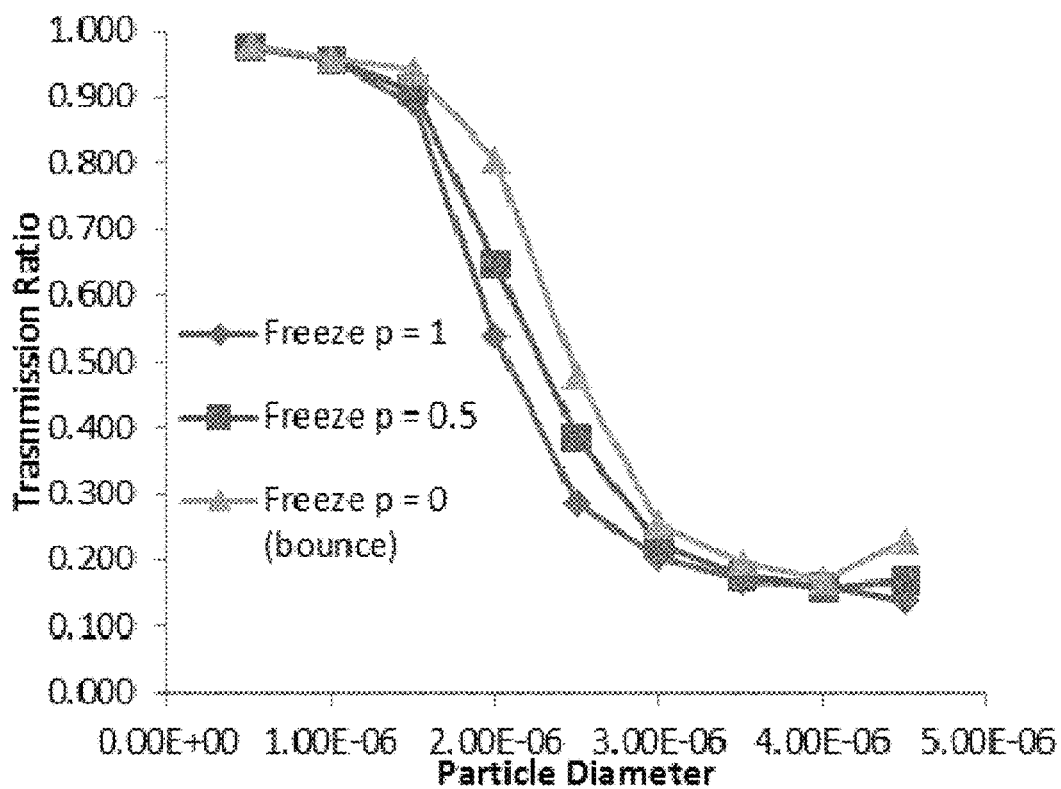

FIG. 21A illustrates an example flow velocity profile for Wi=1.5 Wn according to an example embodiment. FIG. 21B illustrates transmission curve ratios for Wi=1.5 Wn for freeze, 50% freeze and bounce wall conditions.

Figure 22A:
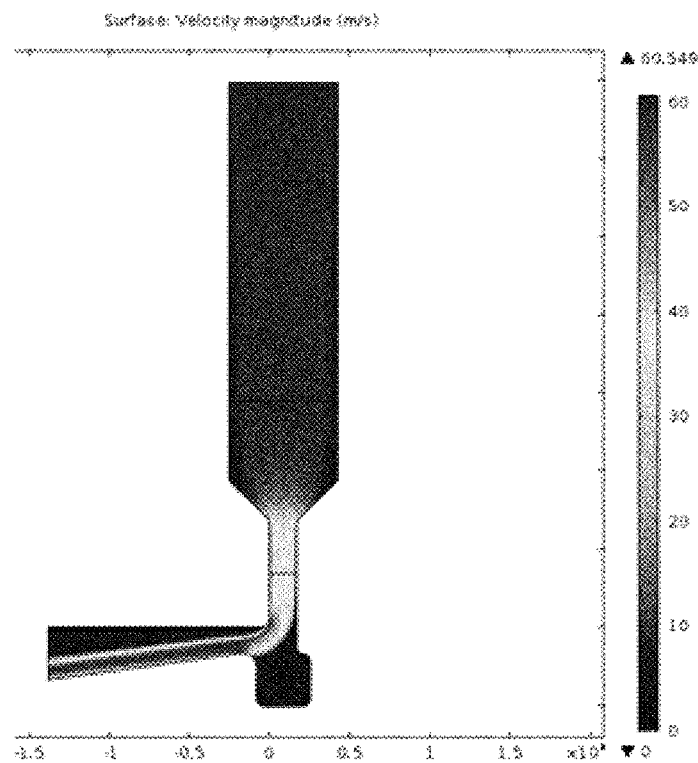
Figure 22B:
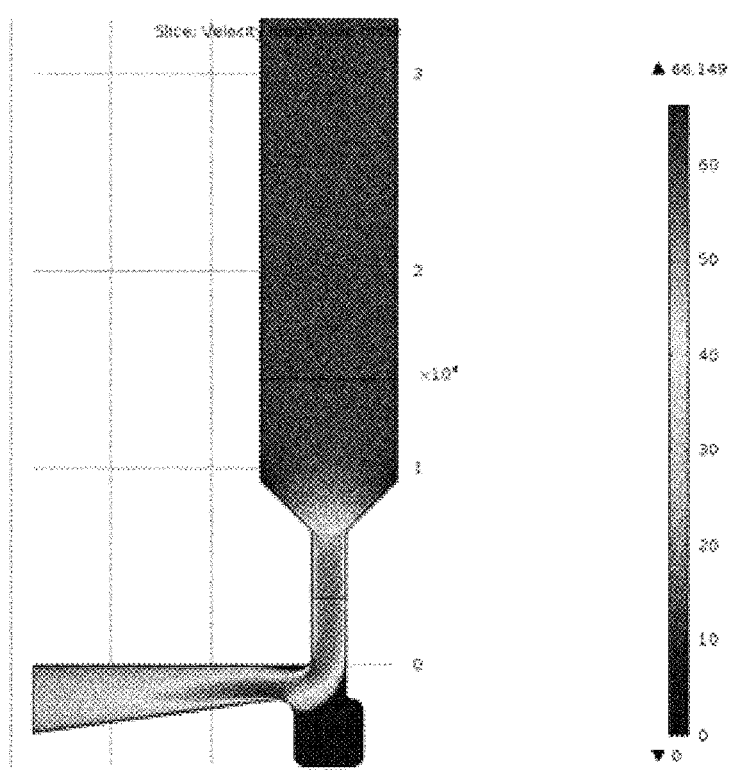

FIGS. 22A and 22B illustrate flow velocity profiles for an example device in 2D and 3D.

Figure 23:
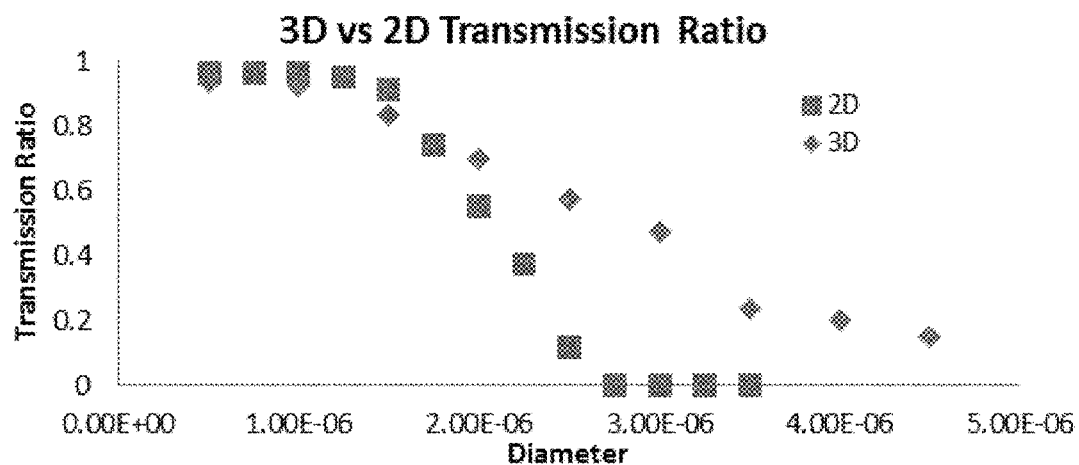

FIG. 23 illustrates transmission ratios for an example impactor in 2D vs. 3D.

Figure 24:
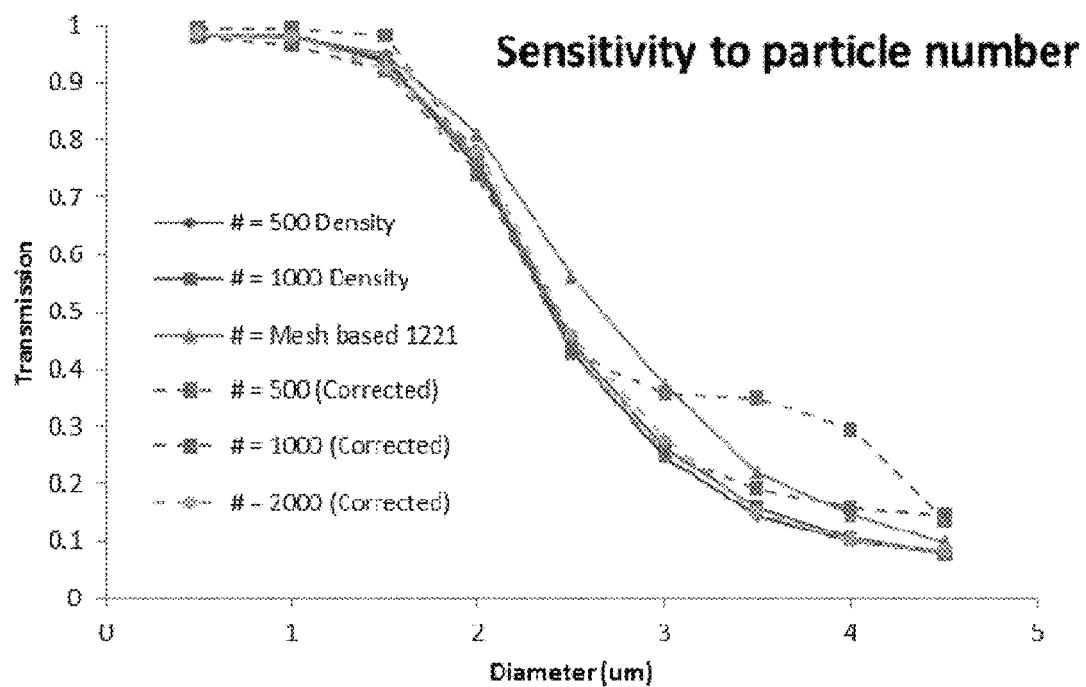

FIG. 24 is a simulated transmission curve for an impactor-type particle monitor for various simulation particle release options (density, mesh and uniform grid).

Figure 25:
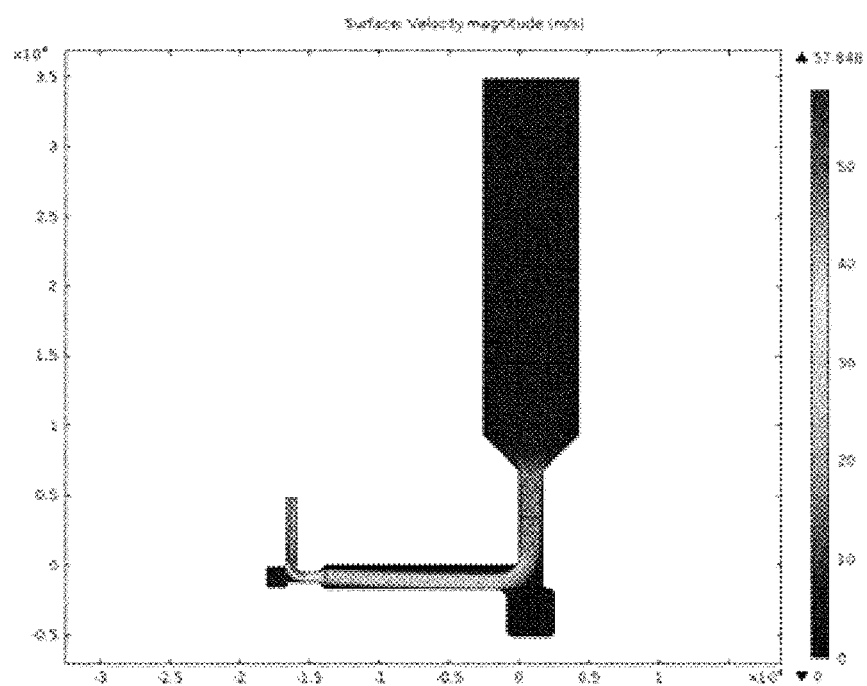
Figure 26:
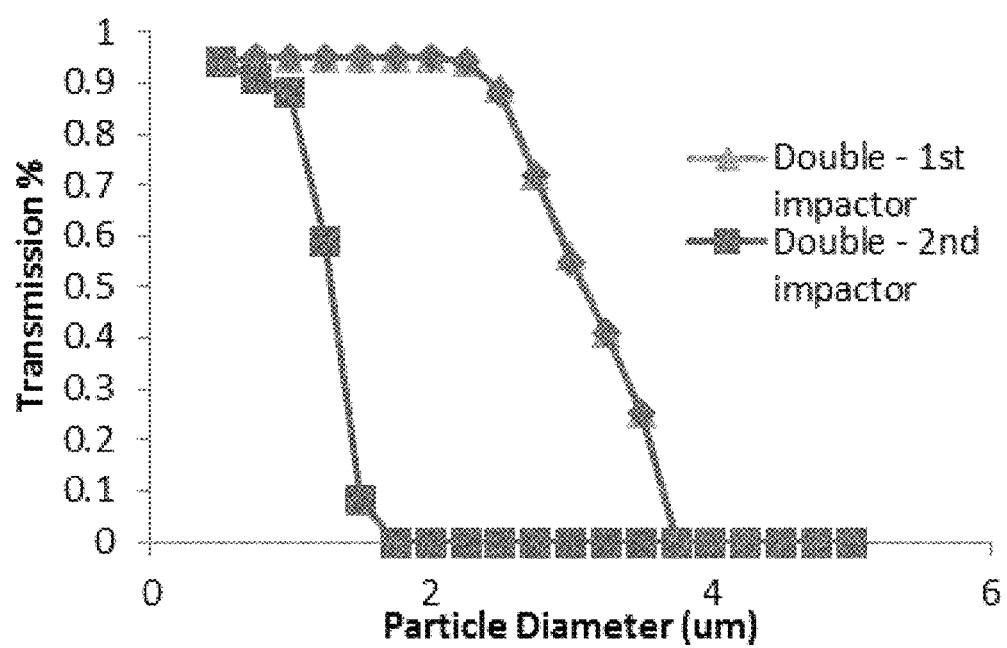
Figure 27A:
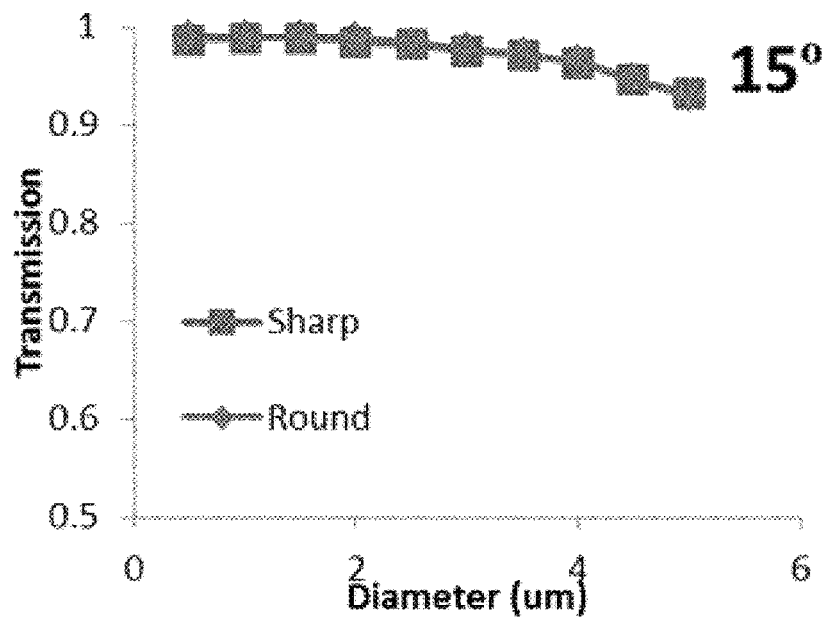
Figure 27B:
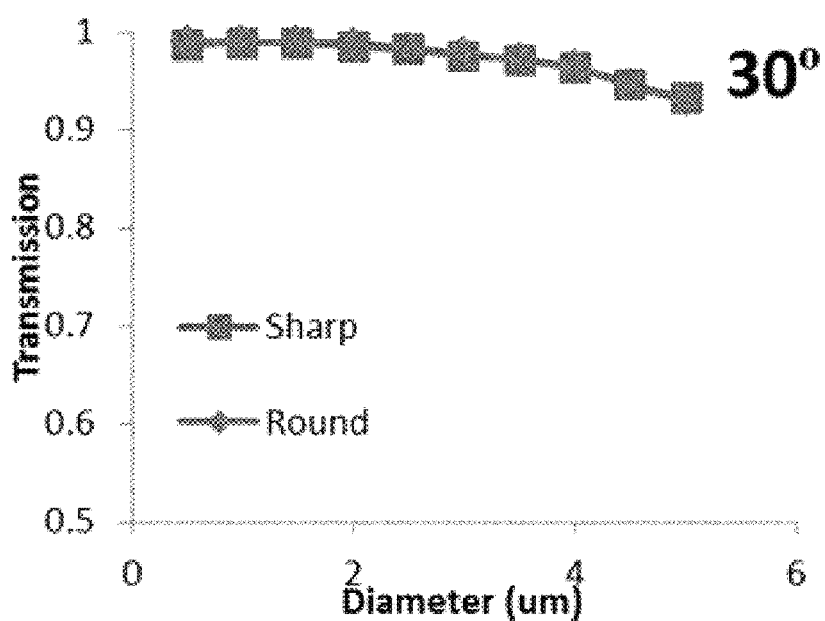
Figure 27C:
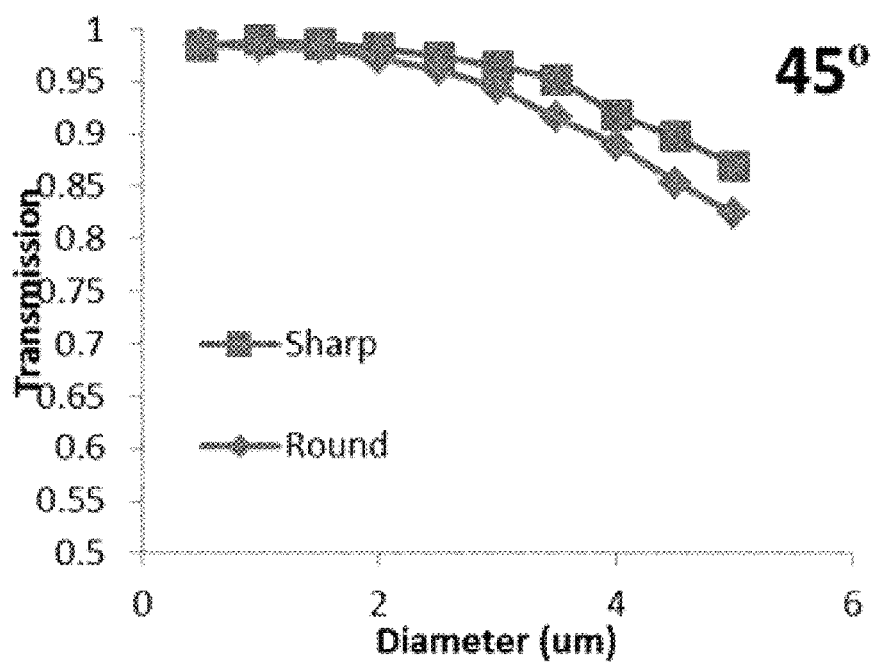
Figure 27D:
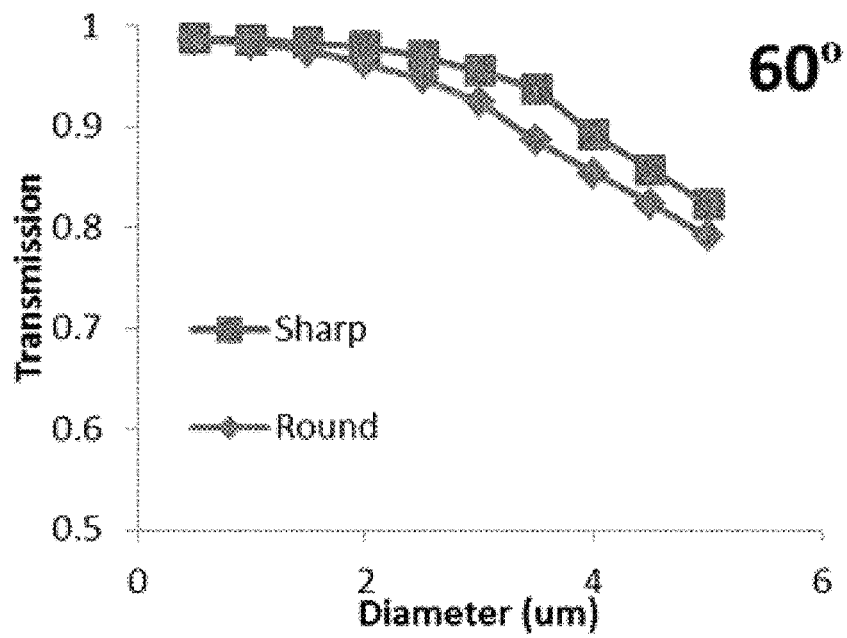
Figure 27E:
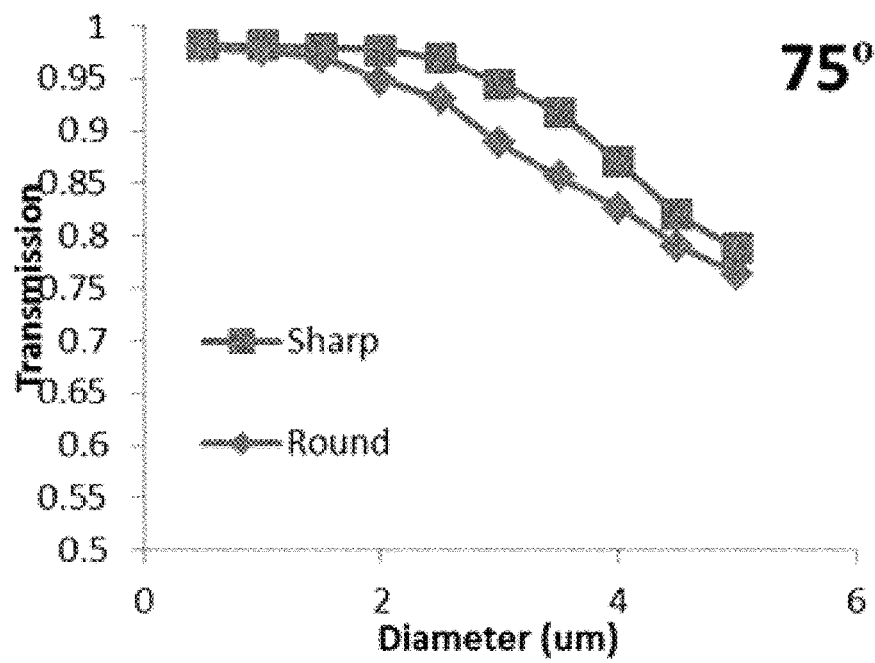
Figure 27F:
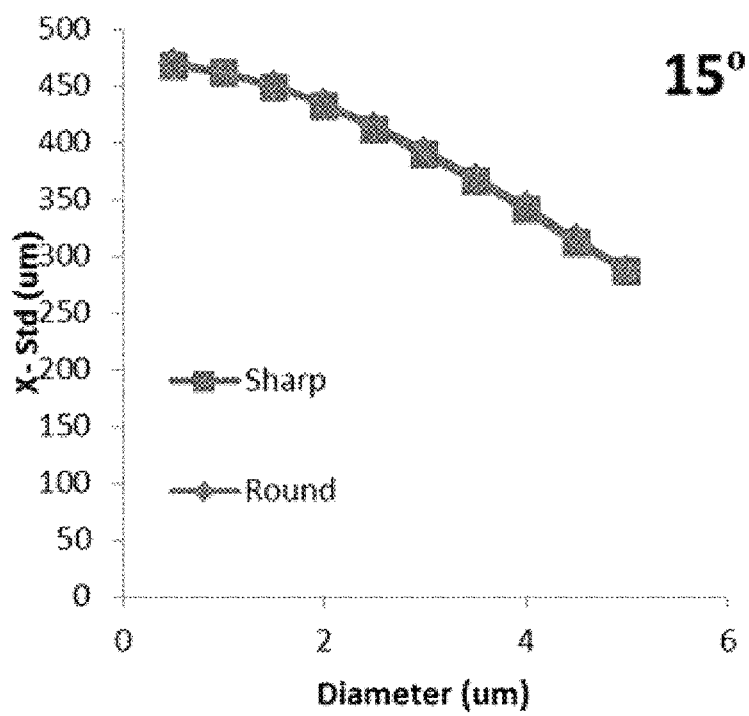
Figure 27G:
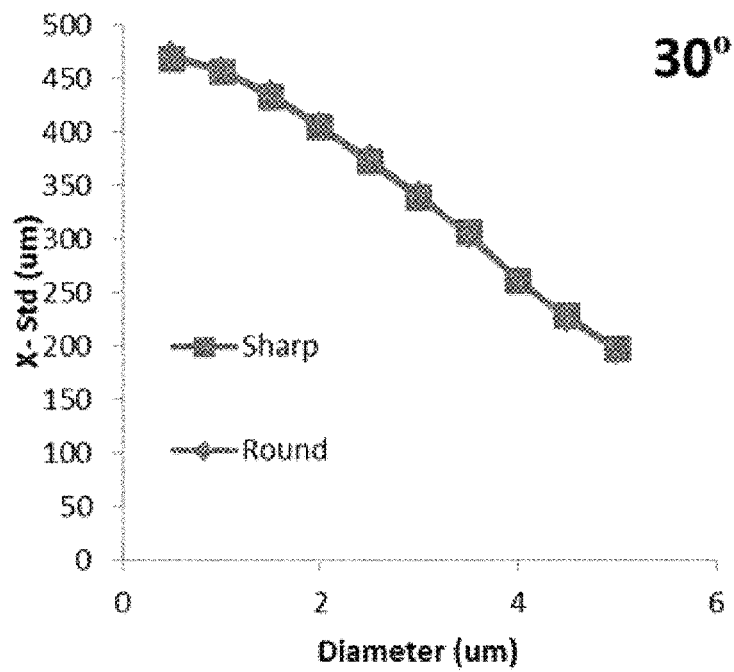
Figure 27H:
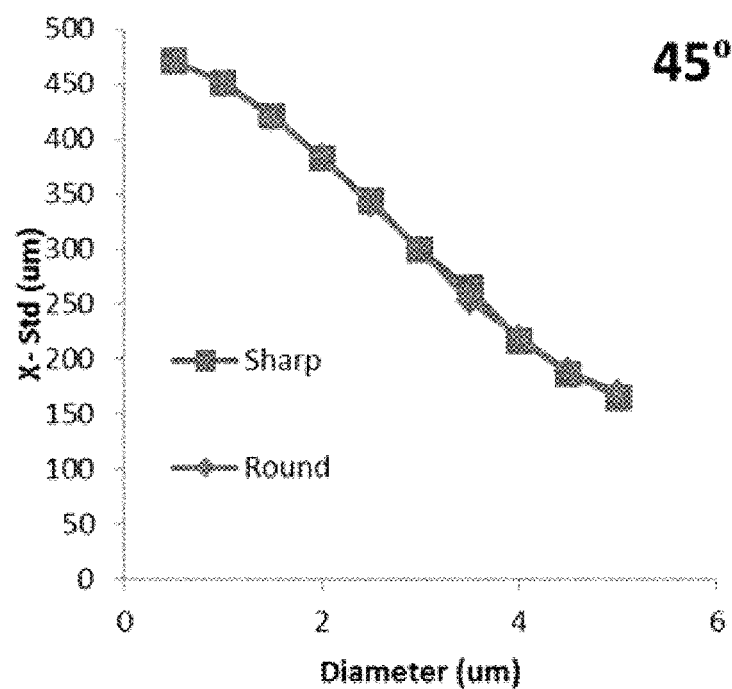
Figure 27I:
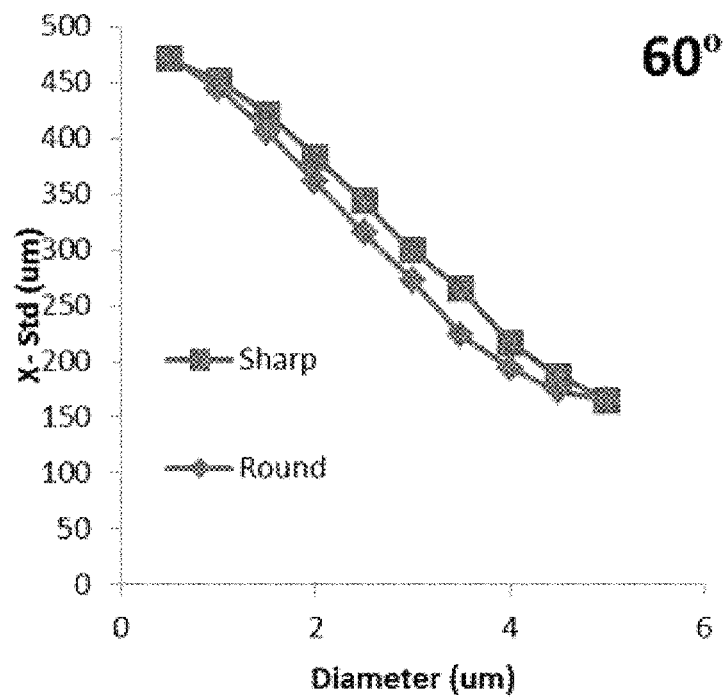
Figure 27J:
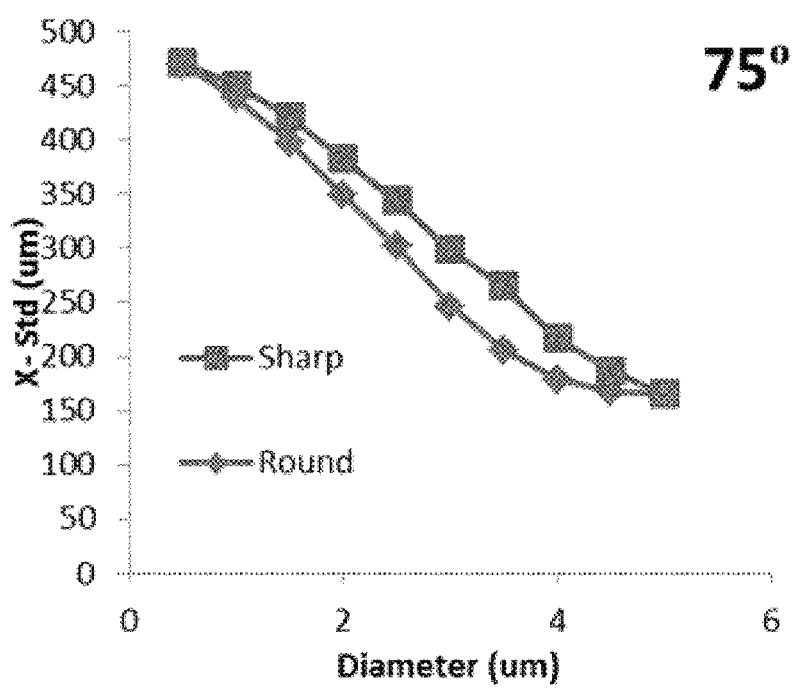

FIG. 25 illustrates a cascading impactor model flow velocity profile according to an example embodiment. FIG. 26 illustrates transmission curve of the cascading particle trap impactor compared to a single stage model according to an example embodiment.

FIGS. 27A to 27J are graphs particle transmission as a function of particle size which illustrate the effect of various angles of taper and different forms for a portion of a flow channel leading into an acceleration nozzle.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

This invention provides methods and apparatus for monitoring particulate matter.

FIG. 1A is a schematic illustration of an example apparatus 100 for monitoring particulate matter according to an example embodiment. Apparatus 100 comprises a defined fluid flow passage 10 and a cartridge 20. Cartridge 20 may be removed and replaced. This may be done, for example, to one or more of:

- change the size range of particles monitored (a range of cartridges that are each designed to monitor for particles of a certain size may be available);
- allow a trade-off between energy consumption and the speed with which measurements or particle concentration are completed (e.g. different cartridges may have flow channels of different cross-sectional areas such that a larger cross sectional area may be used to sample a larger volume of air or other fluid in a shorter time—at the possible expense of shorter battery life in a portable or wearable device);
- replace the cartridge in the event that it becomes clogged or otherwise malfunctions;
- test the contents of the cartridge—for example, in some embodiments a cartridge may retain certain particles in it, in certain applications it may be desired to test these particles for radio activity, chemical composition or the like.

Cartridge 20 comprises a cartridge inlet 30, a cartridge outlet 40, and a particle size selector 50. Cartridge 20 removably interfaces to the rest of apparatus 100.

Apparatus 100 may comprise a particle counter 80 located downstream from particle size selector 50, and a pump 90 connected to drive a flow of fluid 1 containing particulate matter 6 through fluid flow passage 10. In some embodiments, particle size selector 50 comprises a curve section 70 in fluid flow passage 10 in which flowing fluid follows a curve and a particle trap comprising an impact surface 60 extending transversely to the path of the flowing fluid in fluid flow passage 10 on an outside of curve section 70.

Pump 90 is connected to drive the flow of fluid 1 through fluid flow passage 10. Fluid 1 carrying entrained particulate matter 6 enters cartridge 20 through cartridge inlet 30 and travels within fluid flow passage 10 in cartridge 20. In operation, fluid 1 containing entrained particulate matter 6 is drawn into apparatus 100 through a suitable inlet and introduced into fluid flow passage 10. The fluid may, for example, comprise air. The particulate matter may comprise small solid particles and/or liquid aerosols. The particulate matter may comprise particles emitted by vehicles, particles generated by industrial processes etc.

As fluid 1 flows through fluid flow passage 10, particle size selector 50 removes particulate matter 6 of a specific size range or ranges from fluid 1.

In embodiments wherein particle size selector 50 comprises curve section 70 and particle trap which includes impact surface 60, particles 6 of specific sizes are removed from fluid 1 through impacting impact surface 60 and/or becoming trapped in a trapping chamber upstream from impact surface 60. Particulate matter 6 of the desired sizes (which is not trapped or intercepted by impact surface 60) then exits from cartridge 20 through cartridge outlet 40.

In some embodiments, apparatus 100 is capable of monitoring particulate matter 6 that is smaller than 2.5 μm. Larger particles may be removed. In some embodiments, apparatus 100 comprises a filter positioned between cartridge inlet 30 and particle size selector 50. The filter may be configured to remove particles greater than some size cut off (e.g. greater than 10 μm or 20 μm) from fluid 1.

In some embodiments, the cut-off size for particulate matter is controlled by flow rate of fluid 1 in fluid flow passage 10. In some embodiments, the removed particulate matter is collected in a particle trap. In some embodiments, apparatus 100 can detect particulate matter 6 in real-time.

In some embodiments, cartridge inlet 30, cartridge outlet 40, and fluid flow passage 10 are integral to cartridge 20. In some embodiments, these parts are removably connected to cartridge 20. In some embodiments, cartridge 20 has a planar configuration and curve 70 is in a plane of the cartridge.

In some embodiments, fluid flow passage 10 is flattened and has a width that is significantly greater than a height of the flow passage 10 perpendicular to the width. The portion of flow passage 10 which makes up curved section 70 may be configured such that the fluid flow direction turns about an axis that is at right angles to a plane containing flow passage 10. Where cartridge 20 has a planar configuration the width may be in the plane of cartridge 20.

In some embodiments, fluid flow passage 10 comprises an accelerating nozzle immediately upstream from curve 70. In some embodiments, the width of fluid flow passage 10 is reduced in the accelerating nozzle. In some embodiments, fluid flow passage 10 has a width in the accelerating nozzle in the range of about 1400 µm to about 2000 µm. In some embodiments, fluid flow passage 10 has a height in the accelerating nozzle in the range about 150 µm to about 500 µm. In some embodiments, fluid flow passage 10 in the accelerating nozzle has an aspect ratio of width to height in the range of 5:1 to 9:1. In some embodiments, fluid flow passage 10 in the accelerating nozzle has a width of 1700 µm±5% and a height of 200 µm±5% or µm±10%.

In some embodiments, a ratio of the width of fluid flow passage 10 between cartridge inlet 20 and the accelerating nozzle to the width of fluid flow passage 10 in the accelerating nozzle is in the range of 3:1 to 5:1. In some embodiments, fluid flow passage 10 is tapered in width immediately upstream from the accelerating nozzle. The angle of taper is in the range of 22 to 77 degrees in some embodiments— where 0 degrees indicates an angle parallel to the flow passage and 90 degrees indicates an angle perpendicular to the flow passage. The preferred angle is 30 to 60 degrees with 45 degrees being used in some embodiments. In some embodiments, a ratio of a length of the accelerating nozzle to the width of the accelerating nozzle is 3:1 or greater.

In some embodiments, curved section 70 causes the fluid flow to change direction through an angle of at least 60 degrees around an axis defining a radius of curvature of the fluid flow.

In some embodiments, a width of an impingement surface of the accelerating nozzle is greater than the width of the accelerating nozzle. In some embodiments, the width of the impingement surface is at least 1¾ times the width of the accelerating nozzle. In some embodiments, the impingement surface comprises a surface extending parallel to a longitudinal axis of the accelerating nozzle. In some embodiments, the line on which the impingement surface lies is spaced apart from an edge of the accelerating nozzle closest to the outside of the curve by a distance greater than the width of the accelerating nozzle.

In some embodiments, an output end of the accelerating nozzle is directed toward a chamber bounded on one side by the impingement surface. In some embodiments, apparatus 100 comprises one or more fluid ports in the chamber. In some embodiments, apparatus 100 comprises a fluid source connected to one of the one or more fluid ports and a valve operable to allow fluid 1 from the fluid source to enter the chamber. Such ports may be used to purge trapped particles from the trapping chamber on a periodic or continuous basis.

In some embodiments, cartridge 20 comprises a filter in fluid flow passage 10 between the cartridge inlet 20 and the particle size selector 50. In some embodiments, the filter in fluid flow passage 10 is formed in a plastic material which also defines fluid flow passage 10. The filter may be integrally formed with fluid flow passage 10. Such a filter may be applied to prevent certain large particles from reaching the particle size selector.

In some embodiments, portion of fluid flow passage 10 passing through cartridge 20 is molded. In some embodiments, cartridge 20 comprises a sheet of a plastic material and the flow passage 10 is moulded into the plastic material. In further embodiments, the plastic material comprises PDMS.

In some embodiments, cartridge inlet 30 is formed in an edge of cartridge 20 such that a flow of fluid 1 entering cartridge 20 is in line with the flow passage. In some embodiments, cartridge outlet 40 is formed in an edge of cartridge 20 such that a flow of fluid 1 exiting cartridge 20 is in line with the flow passage.

In some embodiments, particle counter 80 is arranged to count particles downstream from cartridge outlet 40. In some embodiments, particle counter 80 is an optical particle counter. In some embodiments, particle counter 80 comprises a light source and a light detector arranged such that light from the light source is received at the light detector after interacting with particles in a light path extending through fluid flow passage 10. In some embodiments, light from the light source is focused onto a light trap and the light detector is arranged to intercept light forward scattered by particles in the portion of the fluid passage 10 through which the light path passes.

In some embodiments, when pump 90 is operating, particle size selector 50 is operative to remove at least 50% of particles having sizes in excess of 5 µm from the fluid 1 flowing through particle size selector 50. In some embodiments, particle size selector 50 is operative to remove at least 50% of particles having sizes in excess of 3 µm or 2.5 µm from fluid 1 flowing through particle size selector 50.

In some embodiments, apparatus 100 comprises a processor connected to receive an output from particle counter 50 and to process the output of particle counter 50 to yield a measure of concentration of particles counted by the particle counter in the fluid 1 flowing in fluid flow passage 10. In some embodiments, apparatus 100 comprises a data logger comprising a processor and a data store. The data logger is connected to receive an output of the particle counter 50 and is operative to record in the data store values indicative of the number of particles counted by particle counter 50 in different time periods. One circuit (which may include one or more programmed data processors in some embodiments) may perform one or more of: data logging functions, computing concentrations or other information based on the output of the particle counter, and controlling operation of apparatus 100 (e.g. operating the apparatus continuously or periodically to count particles) and monitoring the status of apparatus 100 (e.g. monitoring a flow rate when apparatus 100 is operating and/or monitoring a sensor that determines whether a particle trap is becoming full etc.). As an alternative, separate circuits may be provided to perform these functions.

In some embodiments, particle size selector 50 is a first of a plurality of particle size selectors connected in series in the fluid flow path 10 and particle size cut-offs for the particle size selectors decrease sequentially in a downstream direction. Depending on the application, a separate particle counter may be provided downstream from each of the particle size selectors or one particle counter may be provided downstream from the last of the particle size selectors. The cascaded particle size selectors in some embodiments are formed in a single cartridge 20. In other embodiments, the plural particle size selectors are provided in a plurality of cartridges 20. Other embodiments provide plural cascaded particle size selectors as described herein but some or all of the particle size selectors are not provided in replaceable cartridges.

In some embodiments, a first particle counter 80 is arranged to count particles in the fluid flow path 10 between a first particle size selector 50A and a second particle size selector 50B downstream from first particle size selector 50A. A second particle counter may be arranged to count particles downstream from second particle size selector 50B.

In some embodiments, pump 90 has an output of 1 l/min or less for each 200 µm of height of fluid flow passage 10.

In some embodiments, pump 90 has an output of 600 ml/min or less. In some embodiments, pump 90 is battery powered. In some embodiments, apparatus 100 is in a wearable package that comprises a fastener, such as one or more hooks, clips, and the like, for attaching apparatus 100 to clothing of a person.

Apparatus as described herein may have a range of optional features. For example, the apparatus may comprise a sensor that detects when a particle trap is full or nearly full. The sensor may, for example, comprise an optical sensor. A sensor may be connected to trigger an alarm or other indicator to advise a user to replace the cartridge before the reliability of readings becomes compromised.

Figure 1A:
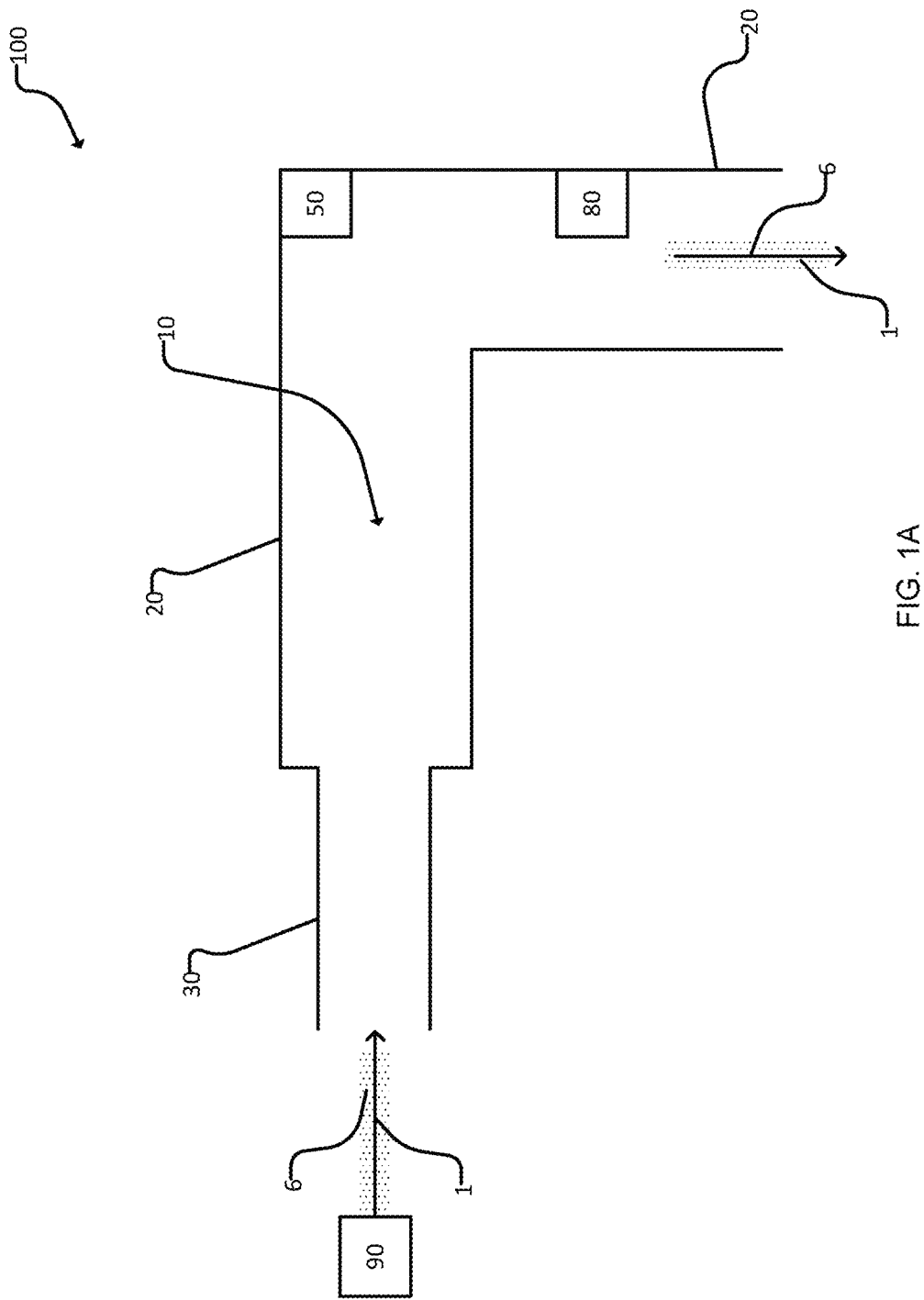
FIG. 1A is a schematic view of an apparatus for monitoring particulate matter according to an example embodiment of the present invention.
Figure 1B:
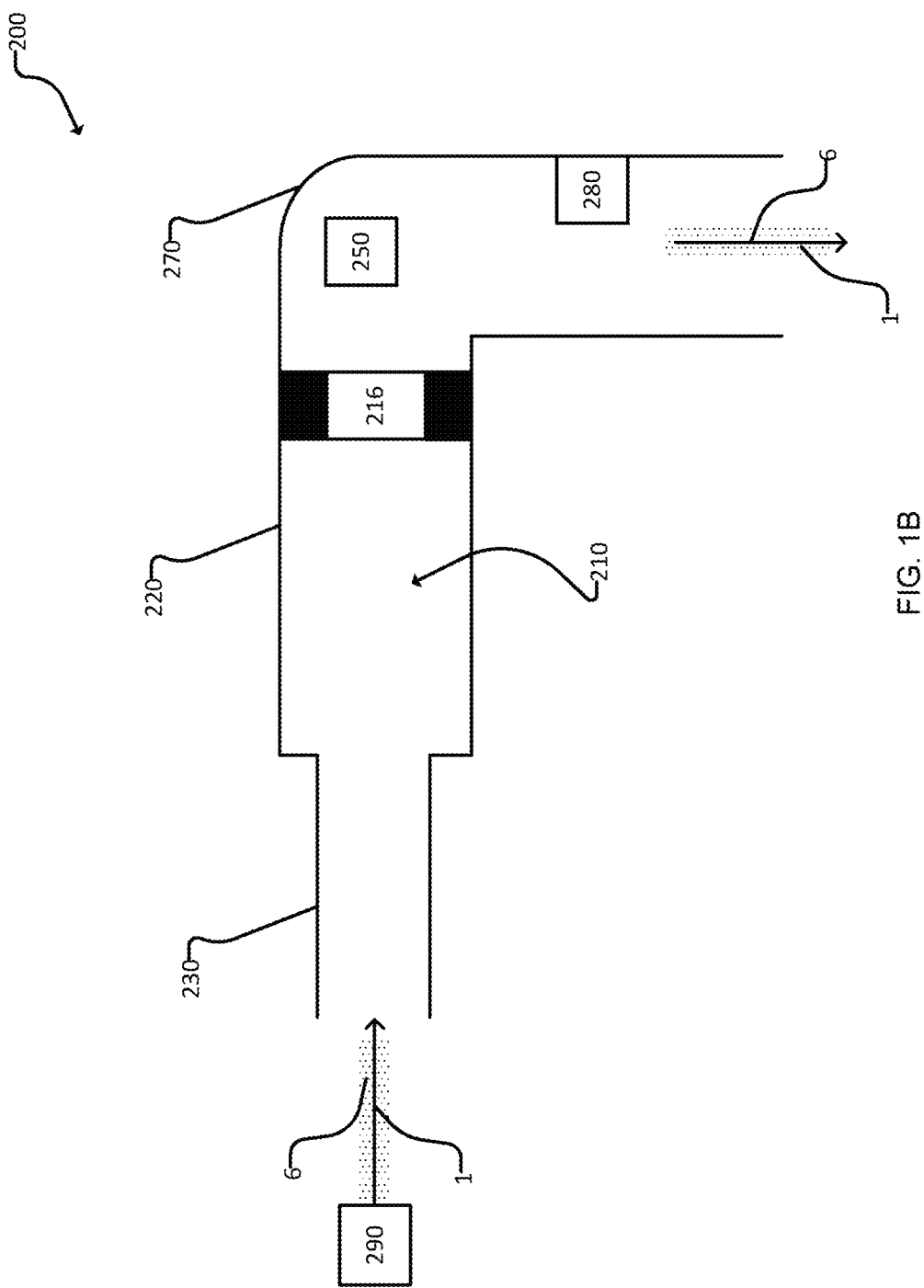
FIG. 1B is a schematic view of an apparatus for monitoring particulate matter according to another example embodiment of the present invention.

FIG. 1B is a schematic illustration of an apparatus 200 for monitoring particulate matter according to another example embodiment. Apparatus 200 is similar to apparatus 100 but does not necessarily have a removable cartridge. Apparatus 200 has an acceleration nozzle that works in conjunction with the particle size selector. Apparatus 200 may optionally include any of the features described above for apparatus 100.

In the illustrated embodiment, apparatus 200 comprises a fluid flow passage 210 having an inlet 230 and an outlet 240, a particle size selector 250 in fluid flow passage 210 between inlet 230 and outlet 240, and particle size selector 250 comprising a curve section 270 in fluid flow passage 210 and an impact surface 60 extending transversely to fluid flow passage 210 on an outside of curve section 270. Apparatus 200 further comprises accelerating nozzle 216 immediately upstream from the location at which fluid flow begins to change direction in curve section 270. The width of fluid flow passage 210 is reduced in the accelerating nozzle 216. Apparatus 200 also comprises particle counter 280 located downstream from particle size selector 250 and a pump 290 connected to drive a flow of fluid 1 containing particulate matter 6 through fluid flow passage 210.

In some embodiments, apparatus 200 has a planar configuration and curve section 270 is in a plane of apparatus 200. In some embodiments, fluid flow passage 210 is flattened and has a width that is significantly greater than a height of fluid flow passage 210 perpendicular to the width.

In some embodiments, accelerating nozzle 216 comprises a parallel-sided passage. In some embodiments, flow passage 210 in accelerating nozzle 216 has a width in the range of 1400 µm to about 2000 µm. In some embodiments, flow passage 210 in accelerating nozzle 216 has a height in the range of 150 µm to 500 µm. In some embodiments, flow passage 210 in accelerating nozzle 216 has an aspect ratio of width to height in the range of 5:1 to 9:1. In some embodiments, flow passage 210 in accelerating nozzle 216 has a width of 1700 µm±5% or ±10% and a height of 200 µm±5% or ±10%.

In some embodiments, a portion of the fluid flow passage 210 between the inlet 230 and the accelerating nozzle 216 has a width greater than that of the accelerating nozzle 216. In some embodiments, a ratio of the width of the fluid flow passage 210 between the inlet 230 and the accelerating nozzle 216 to the width of the fluid flow passage 210 in the accelerating nozzle 216 is in the range of 3:1 to 5:1.

In some embodiments, fluid flow passage 210 is tapered in width immediately upstream from accelerating nozzle 216. In some embodiments, a ratio of a length of accelerating nozzle 216 to the width of the accelerating nozzle 216 is 3:1 or greater.

In some embodiments, a width of the impingement surface is greater than the width of accelerating nozzle 216 (a width of the exit of accelerating nozzle 216 if accelerating nozzle 216 as a variable width. In some embodiments, a width of the impingement surface is at least 1¾ times the width of accelerating nozzle 216. In some embodiments, the impingement surface comprises a surface extending parallel to a longitudinal axis of accelerating nozzle 216. In some embodiments, the line on which the impingement surface lies is spaced apart from an edge of the accelerating nozzle 216 closest to the outside of the curve by a distance greater than the width of accelerating nozzle 216. In some embodiments, an output end of accelerating nozzle 216 is directed towards a chamber bounded on one side by the impingement surface. In some embodiments, apparatus 200 comprises a fluid port in the chamber. In some embodiments, apparatus 200 comprises a fluid source connected to the fluid port and a valve operable to allow fluid 1 from the fluid source to enter the chamber.

In some embodiments, apparatus 200 comprises a filter in the flow passage 210 between the inlet 230 and the particle size selector 250. In some embodiments, apparatus 200 comprises a sheet of a plastic material wherein at least a portion of the flow passage 210 is moulded into the plastic material. In some embodiments, the plastic material comprises PDMS.

In some embodiments, particle counter 280 comprises an optical particle counter.

In some embodiments, particle counter 280 comprises a light source and a light detector arranged such that light from the light source is received at the light detector after interacting with particles in a light path extending through the fluid flow passage 210. In some embodiments, light from the light source is focused onto a light trap and the light detector is arranged to intercept light forward scattered by particles in the portion of the fluid passage 210 through which the light path passes.

In some embodiments, when the pump 290 is operating, the particle size selector 250 is operative to remove at least 50% of particles having sizes in excess of 5 µm from the fluid 1 flowing through the particle size selector 250. In some embodiments, particle size selector 250 may be operative to remove at least 50% of particles having sizes in excess of 3 µm from the fluid 1 flowing through the particle size selector 250.

In some embodiments, apparatus 200 comprises a processor connected to receive an output from the particle counter 280 and to process the output of the particle counter 280 to yield a measure of mass concentration of particles counted by the particle counter 280 in the fluid 1 flowing in the fluid flow passage 210. In some embodiments, apparatus 200 comprises a data logger comprising a processor and a data store, the data logger connected to receive an output of the particle counter 280 and operative to record in the data store values indicative of the number of particles counted by the particle counter 280 in different time periods. In some embodiments, particle size selector 250 is a first of a plurality of particle size selectors connected in series in the fluid flow path 210 and particle size cut-offs for the particle size selectors decrease sequentially in a downstream direction. In some embodiments, particle counter 280 is arranged to count particles in the fluid flow path 210 between the first particle size selector 250A and a second particle size selector 250B downstream from the first particle size selector 250A.

In some embodiments, pump 290 has an output of 1 l/min or less for each 200 µm of height of the flow passage 210. In some embodiments, pump 290 has an output of 600 ml/min or less. In some embodiments, pump 290 is battery powered. In some embodiments, apparatus 200 is provided in a wearable package comprising a fastener for attaching the apparatus to clothing of a person.

Some embodiments provide apparatus capable of satisfying some or all of the following design parameters:

- Able to select for size PM 2.5 particles, the impactor is designed so that 50% of 2.5 μm diameter particles are deposited in the particle trapping region.
- 5 minutes sampling time (or less) for real-time measurement.
- Portable device
- Flow rate is high enough to obtain statistically significant counts (e.g. 500 ml/min) but low enough to be practical for a portable apparatus (e.g. <2 L/min)
- channel height in the range of 100-600 μm
- Small footprint (facilitates wearable device).
- Particle size selector operates in the laminar flow regime (e.g. curved section design does not result in turbulent flow at designed-for flow rates.

The following sections describe details that may optionally be incorporated into the designs of apparatus and methods according to example embodiments, example design approaches that may be applied to design apparatus according to various embodiments as well as results of testing of certain prototype apparatus.

Theory and Design

While the inventors do not wish to be bound by any particular theory of operation, it is currently believed that the following description explains underlying principles of operation of apparatus as described herein.

Detection System Operation Principles

Figure 1C:
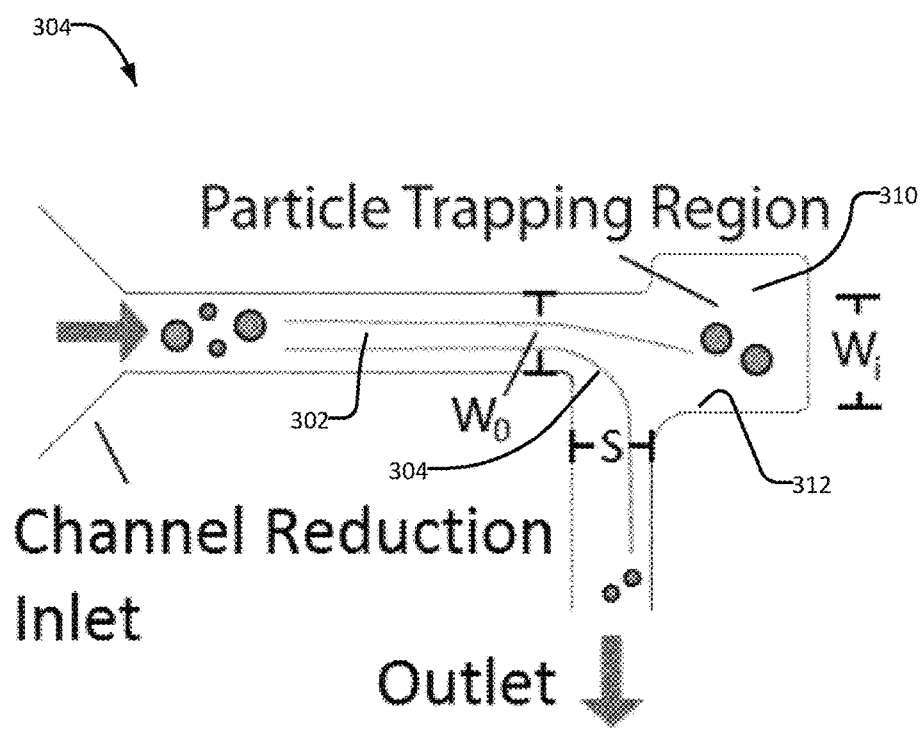
FIG. 1C is an illustration of a particle trap impactor design according to an example embodiment.

FIG. 1C shows an example impactor-type particle size selector 300 which may be called a "microfluidic impactor". In apparatus 300 a sample air stream 302 is directed around a sharp turn 304. In the illustrated embodiment the direction of fluid flow changes sharply at turn 304. In the illustrated embodiment the fluid flow direction changes by 90° in a tight-radius turn. This angle is not necessarily 90 degrees but could be larger or smaller than 90 degrees. In some embodiments the angle is in the range of 70 to 135 degrees. Other embodiments may have turns through larger or smaller angles.

Particles transported with the air or other fluid flowing in apparatus 300 experience a centrifugal force at the turn, causing them to move outwards radially to cross the fluid streamlines. This motion is opposed by the viscous drag force. For particles larger than a cut-off diameter, the inertia force dominates such that the particles enter into a particle trapping region 310 where they are trapped. Particle trapping region 310 is defined on its downstream side by an impact surface 312. Particles smaller than the designed cut-off diameter follow the flow streamlines to exit the device. The cut-off particle size may be defined as the size for which 50% of the particles are removed from the air sample as the sample flows about turn 304.

Figure 2:
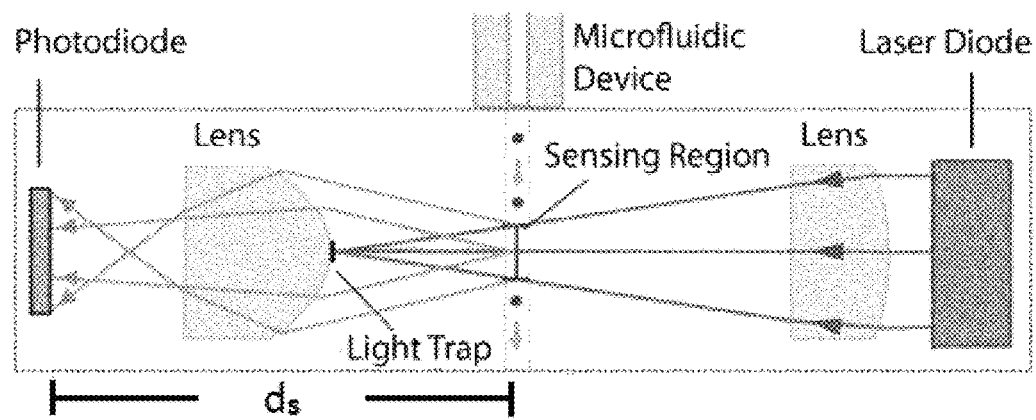
FIG. 2 is an illustration showing a forward light scattering optical detection system layout as may be applied in some embodiments.

The particles exiting the impactor 300 are counted with a particle counter such as a forward light scattering detector. In an example of such a detector, a light beam (e.g. from a laser diode or other suitable light source) is focused by a lens onto the path of the particles forming the sensing region. The light scattered by the particles in this region reaches a second lens from where it is directed onto a photodetector to register a pulse per particle. The number of light pulses may be correlated to a certain concentration such as a PM 2.5 concentration. A light trap prevents the laser light from reaching the photodetector directly which would saturate the photodetector and therefore dominate the signal from the particles. (FIG. 2). He light trap may conveniently be located on the collection lens.

Example Particle Trap Impactor Design

The flow rate may be chosen to be low—so as to reduce power requirements—while being high enough to ensure that the detector count at low designed-for particle concentrations provides statistically significant measurements. In some embodiments the flow rate is less than 1 l/min (1 LPM). For example, a prototype device was designed for a flow rate of 0.5 LPM to ensure results with ±5% error at 95% confidence level within a measurement period of one minute for a minimum designed-for particle concentration. Particle counting may be modelled with the Poisson process. In an example prototype case the flow rate is set to be 500 ml/min to obtain measurement accuracy within ±5% or ±0.5 μg/m³ at 1 μg/m³ detection limit and 5 minutes sampling.

Reference [9] provides some general design considerations for particle size selectors that may be applied to design particle trap impactors for used in embodiments of the apparatus described herein.

Appropriate channel height and the nozzle width for a particle trap impactor may be determined based on the dimensionless Stokes and Reynolds numbers. The Stokes number describes how well the particles follow the fluid streamlines and is given by $$Stk = \frac{\rho_p C v D_p^2}{9 \mu W_o} \quad (1)$$

for an impactor where $\rho_p$ is the particle density, C is the Cunningham slip correction factor, v is the flow velocity, $D_p$ is the particle diameter, μ is the dynamic viscosity of the fluid (e.g. air) and $W_o$ is the nozzle width. The square root of the Stokes number $\sqrt{Stk_{50}}$ may be defined as the value in (1) at which $D_p$ represents the particle diameter for which 50% of the particles are captured. $\sqrt{Stk_{50}}$ is a function of the Reynolds number. In some embodiments. $\sqrt{Stk_{50}}$ is in the range of 0.45 to 0.8.

The Reynolds number is defined as $$Re = \frac{\rho v D_H}{\mu} \quad (2)$$

where ρ is the fluid density and $D_H$ is the hydraulic diameter given by 2ab/(a+b) for a rectangular channel with a width a and a height b. The Reynolds number at the nozzle is recommended to be between 500-3000 for a sharp size cutoff.

In a prototype device, the channel height and the nozzle width were set at 200 μm and 1700 μm respectively to satisfy these initial design guidelines. The prototype provided a 50% cut-off diameter of 2.5 μm at a flow rate of 0.5 LPM.

Particles making a turn as occurs in a curve section of apparatus as described herein will experience an inertial force, causing the particles to cross streamlines in the flow. The inertial force is opposed by a viscous drag force which is given by Stoke's law for small particles. Since the particle velocity in the tangential direction is assumed to be the same as the flow and the U in the drag term is the relative velocity difference between the fluid and the particle, the terminal velocity of the particle is in the radial direction. The velocity can be solved by equating the two forces as shown in equation (3). The velocity is proportional to the square of the particle diameter.

$$U = \frac{1}{18}\left(\frac{\rho d_p^2 V^2}{r\mu}\right) \quad (3)$$

Figure 8:
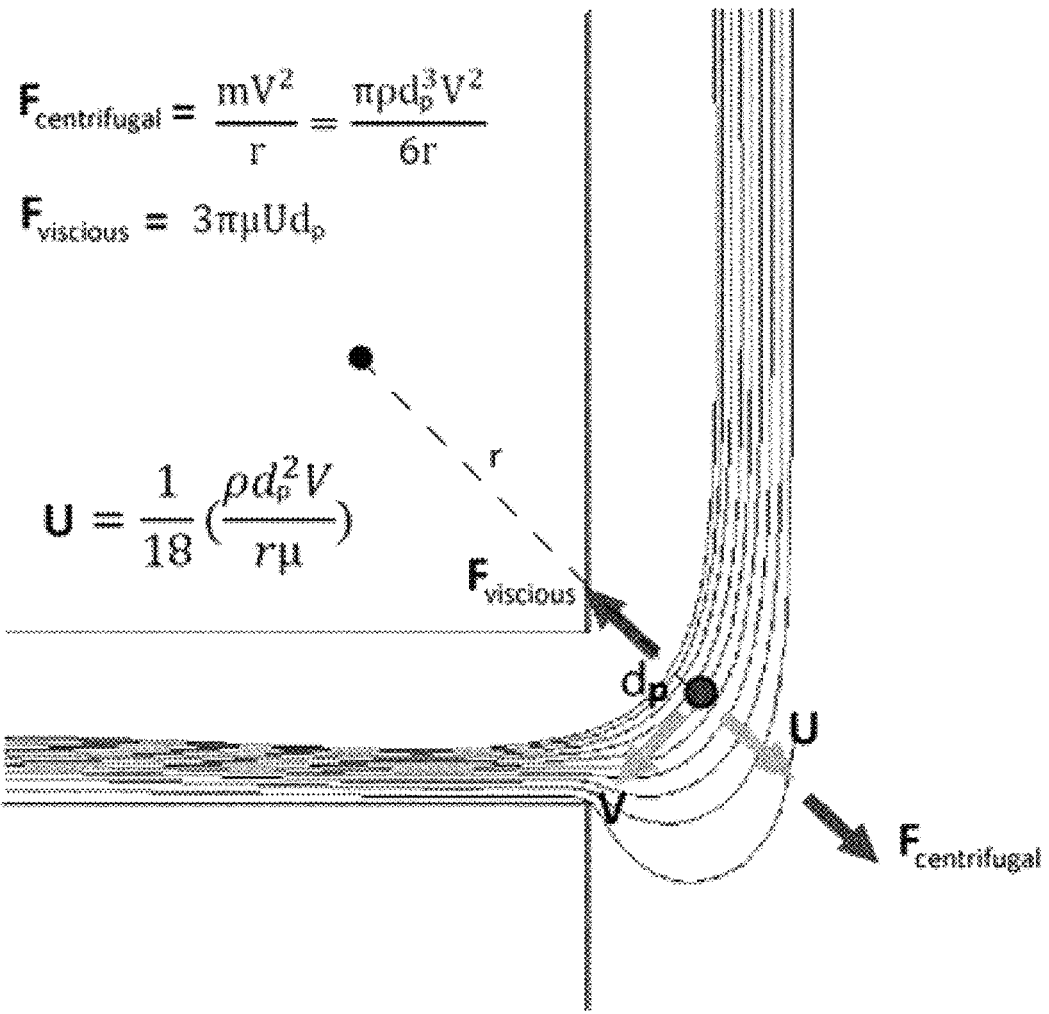

As the particle diameter increases, the particle velocity, U, in the radial direction will increase such that a larger proportion of particles will be driven out of the flow of particles and into the particle trap region on the outside of the curve (see FIG. 8). If the particles are large enough, essentially all of the particles will be trapped before they can be swept around the turn.

Analytical Expression for Particle Radial Displacement

Knowing the radial velocity U from equation 3 and assuming the particle velocity is uniform for all streamlines in the channel, the radial displacement of particles can be roughly estimated by:

$$\Delta d = U*t = \frac{1}{18}\left(\frac{\rho d_p^2 V^2}{r\mu}\right)\frac{2\pi r}{4}\frac{1}{V} = \frac{\pi}{2}\frac{\rho d_p^2 V}{18\mu} \quad (4)$$

where U is the radial velocity and t is the time it takes the particles to travel around the bend. Time t is given by the path of the particle, which is a quarter of the circumference for a 90° bend, and the tangential velocity of the particle. The radial displacement is independent of the radius of curvature of the particle path.

TABLE 1

Radial displacement of particle after 90 degrees bend at average flow velocity of 30 m/s

| dp (um) | Δd (μm) |
|---|---|
| 0.5 | 36 |
| 1 | 145 |
| 1.5 | 325 |
| 2 | 579 |
| 2.5 | 904 |
| 3 | 1302 |
| 3.5 | 1772 |
| 4 | 2314 |
| 4.5 | 2929 |
| 5 | 3616 |

The same calculation can be repeated for other outlet angles which would change the length of time it takes for the particles to be in the bend. For a small outlet bend angle, the time would be shorter so the displacement would be smaller. Conversely, if the outlet angle is larger, the displacement would be greater.

TABLE 2

Radial displacement of particle after 45 and 135 degrees bend at average flow velocity of 30 m/s

| dp (um) | Δd (μm) | |
|---|---|---|
| | 45° | 135° |
| 0.5 | 18 | 54 |
| 1 | 72 | 217 |
| 1.5 | 163 | 488 |
| 2 | 289 | 868 |
| 2.5 | 452 | 1356 |
| 3 | 651 | 1953 |
| 3.5 | 886 | 2658 |
| 4 | 1157 | 3471 |
| 4.5 | 1464 | 4393 |
| 5 | 1808 | 5424 |

Analytical Expression for Transmission Ratio of Impactor

For each flow streamline along the width of the channel, if the radial displacement is greater than the distance between the particle and the particle trapping region, the particles can be assumed to enter the particle trapping region and are removed from the flow. As such, the efficiency is estimated by the expression $$E = 1 - \frac{\Delta d}{S}$$

where S is the width of the outlet. Setting S to be equal to the nozzle width, the transmission ratio of the particle trap impactor for outlet angle 45°, 90° and 135° is computed.

TABLE 3

Transmission ratio of impactor with S = nozzle width, average velocity = 30 m/s for impactor outlet angle 45, 90 and 135 degrees

| dp (um) | E | | |
|---|---|---|---|
| | 45° | 90° | 135° |
| 0.5 | 0.99 | 0.98 | 0.97 |
| 1 | 0.96 | 0.91 | 0.87 |
| 1.5 | 0.90 | 0.81 | 0.71 |
| 2 | 0.83 | 0.66 | 0.49 |
| 2.5 | 0.73 | 0.47 | 0.20 |
| 3 | 0.62 | 0.23 | 0 |
| 3.5 | 0.48 | 0 | 0 |
| 4 | 0.32 | 0 | 0 |
| 4.5 | 0.14 | 0 | 0 |
| 5 | 0 | 0 | 0 |

This model assumes the particles are uniformly distributed along the channel with the same velocity. Particles are typically faster in the center of the channel and slower near the walls due to the parabolic flow profile. As expected, increasing the outlet angle shifts the transmission curve to the left since the radial displacement of the particle increases so smaller particles are trapped.

Figure 9:
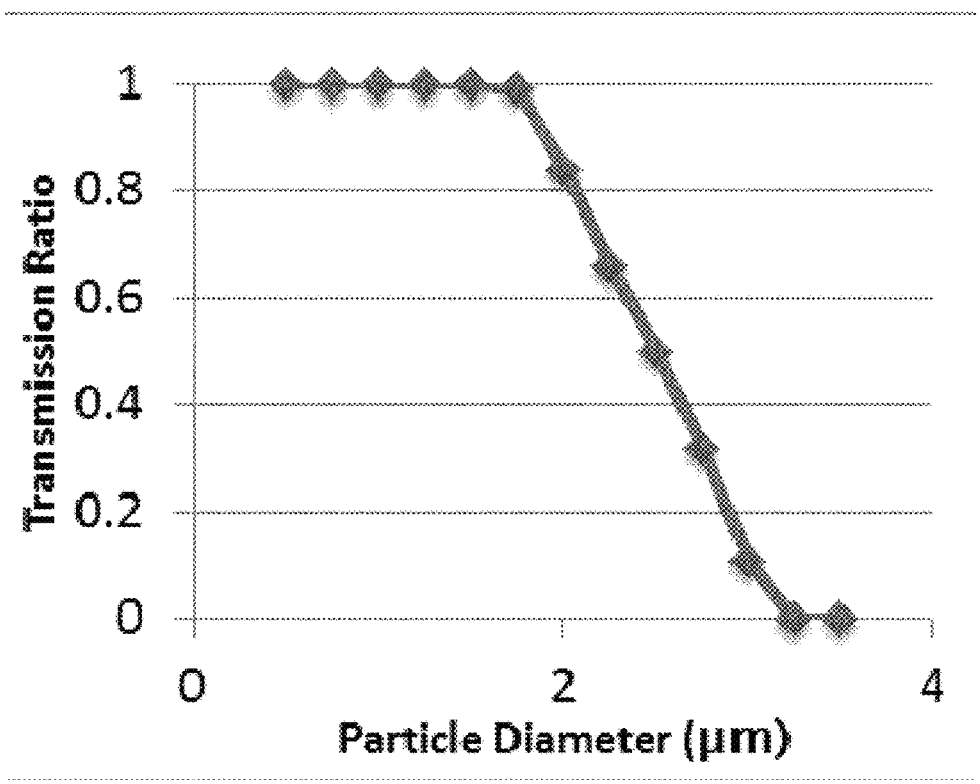
Figure 10:
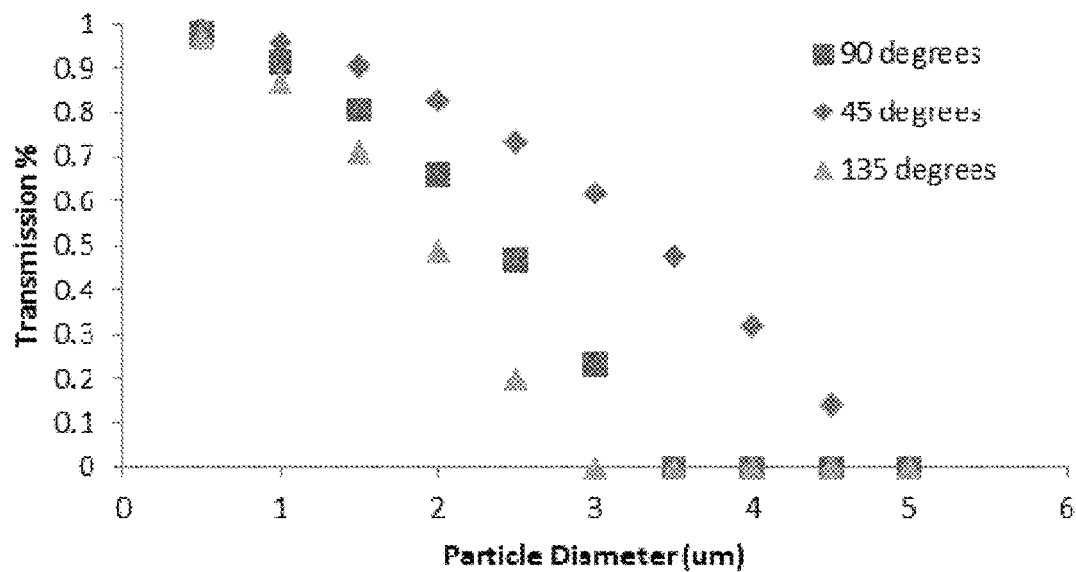
Figure 11A:
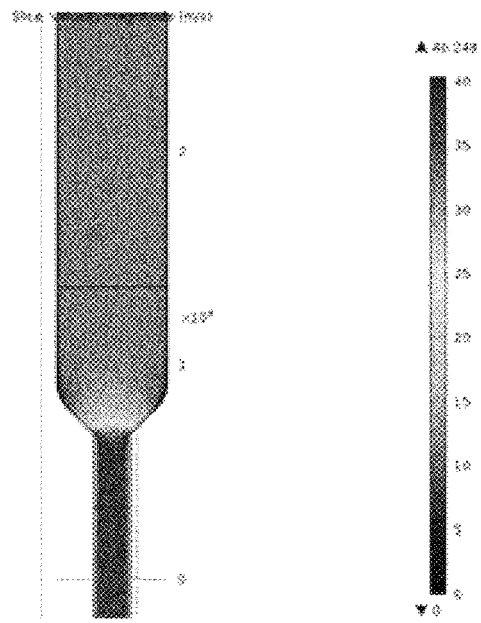
Figure 11B:
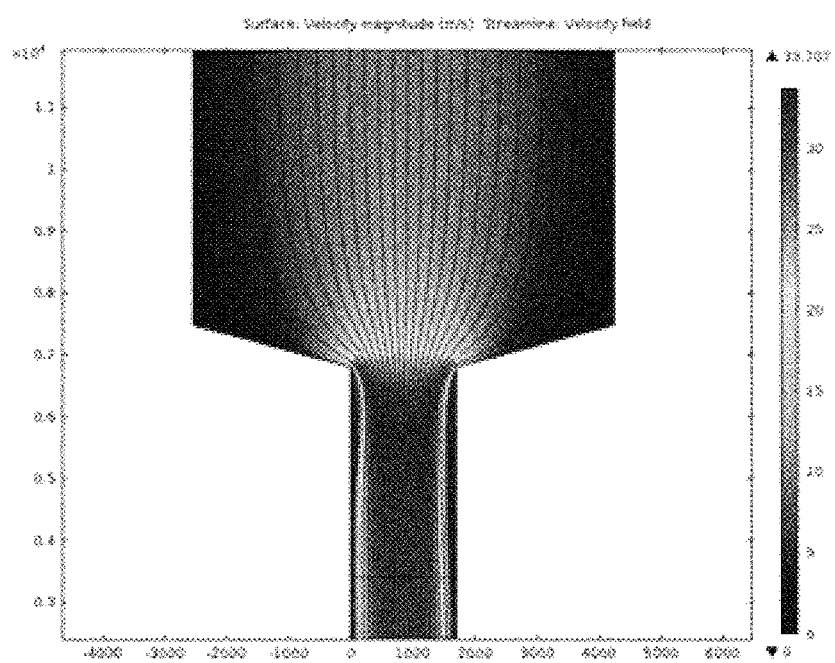
Figure 12A:
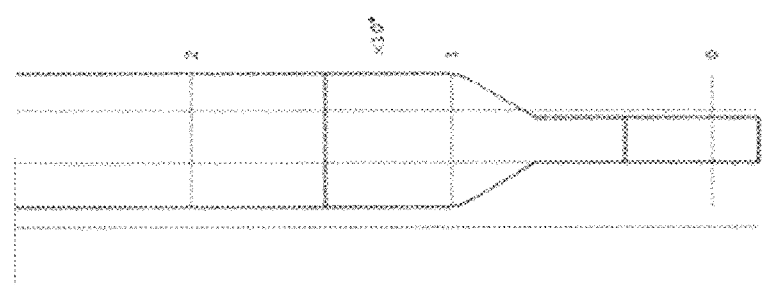
Figure 12B:
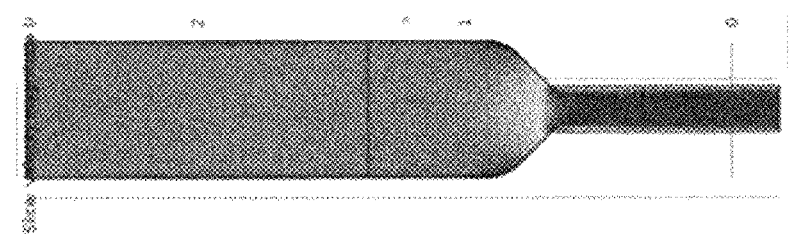
Figure 12C:
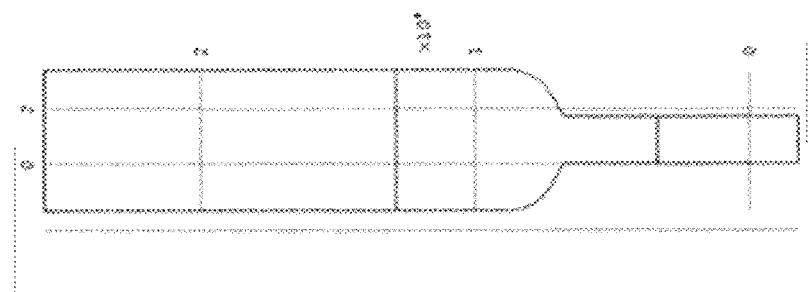
Figure 12D:
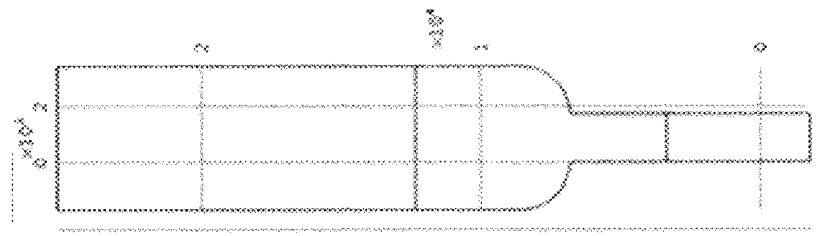
Figure 13A:
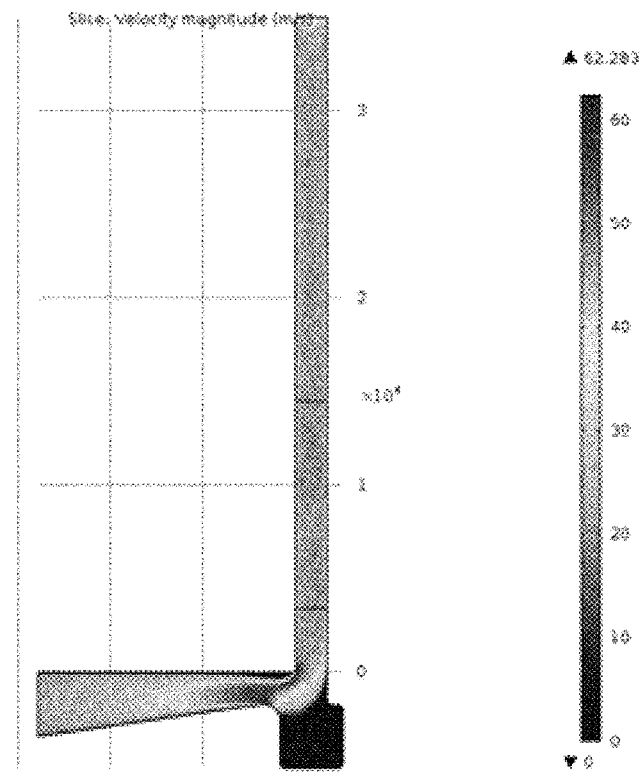
Figure 13B:
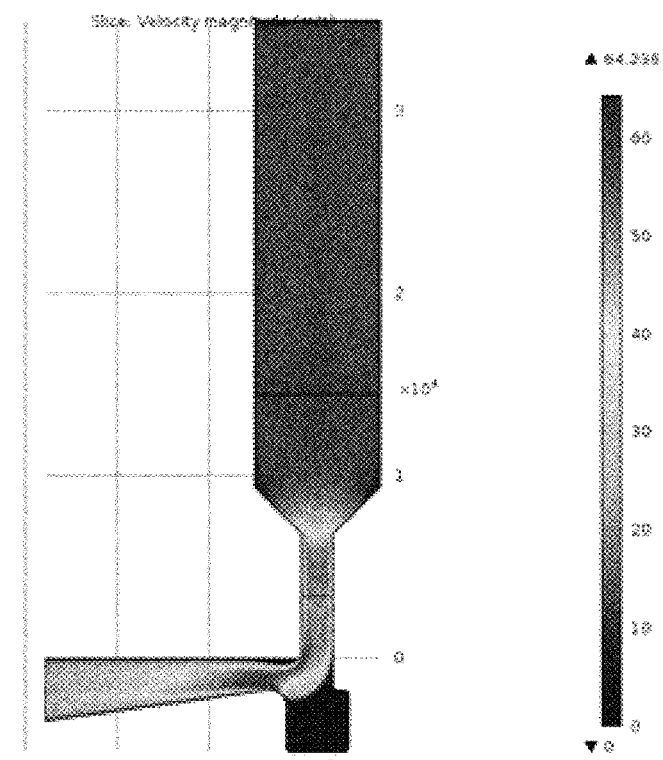

The performance of a particle size selector can be evaluated by the sharpness of the particle transmission curve slope. A sample transmission curve is shown in FIG. 9. The transmission curve of an ideal device would have a vertical straight line at the desired cut-off diameter, indicating all particles less than that size are passed through the device and all particles larger than that size are transmitted.

The particle cut-off characteristics of prototype impactors as described herein have been simulated using Comsol™ Multiphysics (v4.3b). In these simulations, the flow field within the impactor was first solved using the Laminar Flow module by setting the 0.5 LPM flow rate inlet boundary condition. Particles were released uniformly at the inlet with the Particle Tracing module and the number of particles transmitted to the outlet was computed for particle sizes from 0.5 μm to 4 μm. The geometry of the particle trap impactor such as the impactor width W, and nozzle to impactor distance S (FIG. 1) were tuned iteratively to optimize the shape of the impactor cut-off curve. An inertial particle focusing stage (an accelerating nozzle) was also introduced upstream from the particle trap to accelerate and focus the particles towards the center of the channel, preventing large particles from travelling on slow streamlines near the side wall, improving size selectivity.

Example Optical Detector Design

The light scattering behavior for particles larger than the wavelength of light, in the case of particles in the most relevant range from 0.5 μm to 2.5 μm, is described by the Mie theory [10]. Classical optics can be applied in this scattering regime where the particles diffract, reflect and refract the incident light. The angular dependency of the scattered light intensity for 0.5 μm to 2.5 μm particles was computed using the MiePlot software package [11] (v4.3, Philip Laven) to estimate the requirements of the optical system. The detection system in a prototype embodiment was designed to capture the diffraction-dominated forward scattering angle (0°-20° for 2.5 μm particles) where the scattered light intensity is highest and independent of the optical properties of the particles. The alignment of the optical components was designed with OSLO ray tracing software (Lambda Research). The distance between the sensing region and detector $d_s$ (FIG. 2) was minimized due to the inverse-square relationship between the scattered light intensity and the distance between the particle and the detector. However, the light trap will block a large portion of the scattered light if the sensing region is too close to the collection lens. The distance was set such that the light trap does not block more than 5° of the scattered light. The laser diode lens was positioned so the laser diode light was focused on the light trap.

Simulations

Acceleration Inlet

An inertial particle focusing inlet is added before the impactor to improve the sharpness of the cut-off curve. Various angles were simulated in Comsol™ to determine the best design based on particle loss and standard deviation of particle position. The effects of sharp and round corners were also compared.

Increasing the angle increases the inertial focusing affects. However, particles near the side walls are impacted into the inlet wall if the angle is too large as slow velocity vortices are able to form near the corner. An inlet angle of 45 degrees was chosen to provide good focusing and acceptable particle loss for particles less than 2.5 μm in size.

Near the corners of the focusing inlet, a region of low flow velocity field can be observed as shown in FIG. 11. A rounded corner introduces a larger low velocity region, resulting in more particle loss at small focusing angles. However, rounding the corners at large focusing angle would reduce the low velocity region, lowering particle loss.

Larger inlet width provides better focusing. However, particle loss by impaction becomes significant near the channel walls if the width is too large. The channel reduction width is currently set at 4 to 1.

Nozzle Length

The flow velocity is accelerated after the channel constriction at the acceleration inlet. The amount of time required for the particle velocity to reach the fluid velocity is defined as the relaxation time of the particle, τ. For particles smaller than 1 μm, this is given by the Stoke's Drag $$F_D = m_p a = 3\pi\mu d_p V \quad (5)$$

$$m_p x'' = -3\pi\mu d_p x' \quad (6)$$

$$V_p(t) = V_{fluid}(1 - e^{-t/\tau}) \quad (7)$$

$$\text{where } \tau = \frac{18\mu}{\rho d_p^2} \quad (8)$$

The acceleration distance of the particle can be computed by integrated equation (9).

(9)

$$X_p = \frac{\rho d_p^2}{18\mu} V_{fluid}(1 - e^{-t/\tau}) \quad (9)$$

This expression may be used as a design guideline for the nozzle length since the nozzle length should be longer than the acceleration distance required for the particle to reach a steady state velocity before the 90° turn.

TABLE 1

Acceleration distance for 0.5 um to 5 um diameter for flow velocity from 10 to 100 m/s

| | Xp (um) Flow velocity (m/s) | | | | | | | | | |
|---|---|---|---|---|---|---|---|---|---|---|
| dp (μm) | 10 | 20 | 30 | 40 | 50 | 60 | 70 | 80 | 90 | 100 |
| 0.5 | 8 | 15 | 23 | 31 | 38 | 46 | 54 | 61 | 69 | 77 |
| 1 | 31 | 61 | 92 | 123 | 153 | 184 | 215 | 246 | 276 | 307 |
| 1.5 | 69 | 138 | 207 | 276 | 345 | 414 | 483 | 552 | 622 | 691 |
| 2 | 123 | 246 | 368 | 491 | 614 | 737 | 859 | 982 | 1105 | 1228 |
| 2.5 | 192 | 384 | 576 | 767 | 959 | 1151 | 1343 | 1535 | 1727 | 1918 |
| 3 | 276 | 552 | 829 | 1105 | 1381 | 1657 | 1934 | 2210 | 2486 | 2762 |
| 3.5 | 376 | 752 | 1128 | 1504 | 1880 | 2256 | 2632 | 3008 | 3384 | 3760 |
| 4 | 491 | 982 | 1473 | 1964 | 2455 | 2947 | 3438 | 3929 | 4420 | 4911 |
| 4.5 | 622 | 1243 | 1865 | 2486 | 3108 | 3729 | 4351 | 4972 | 5594 | 6215 |
| 5 | 767 | 1535 | 2302 | 3069 | 3837 | 4604 | 5371 | 6139 | 6906 | 7673 |

As seen from the simulations, the flow velocity can reach up to 65 m/s. The nozzle length is set to be 4 times the nozzle width (6800 μm) to provide a sufficient distance to accelerate.

Figure 14:
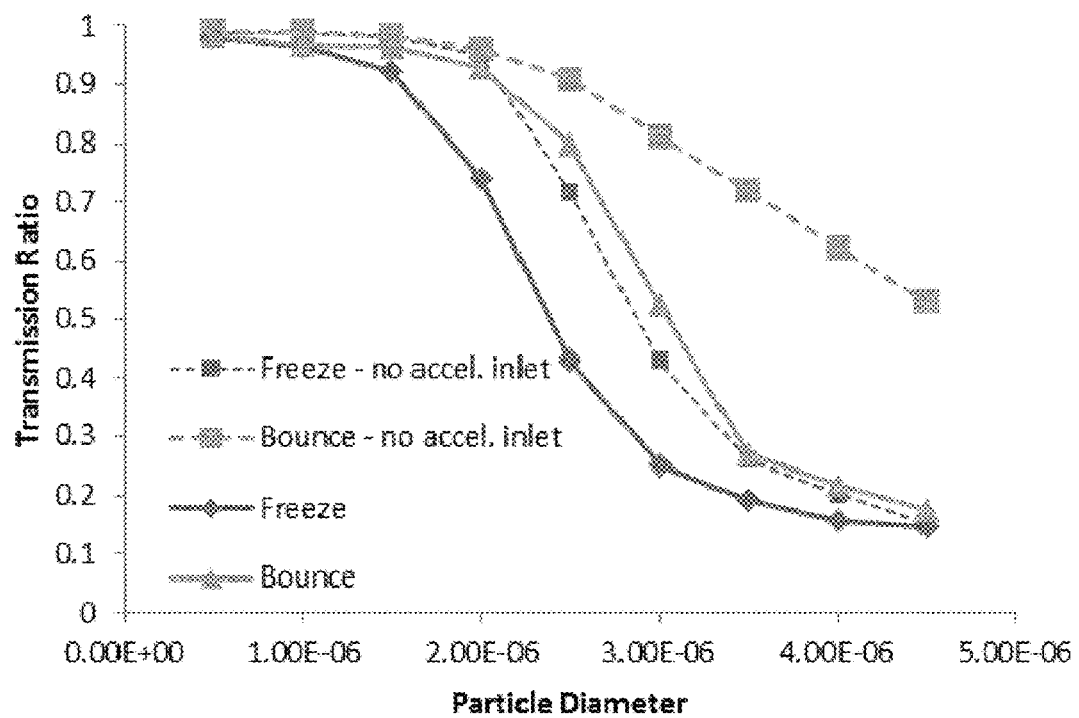
Figure 15:
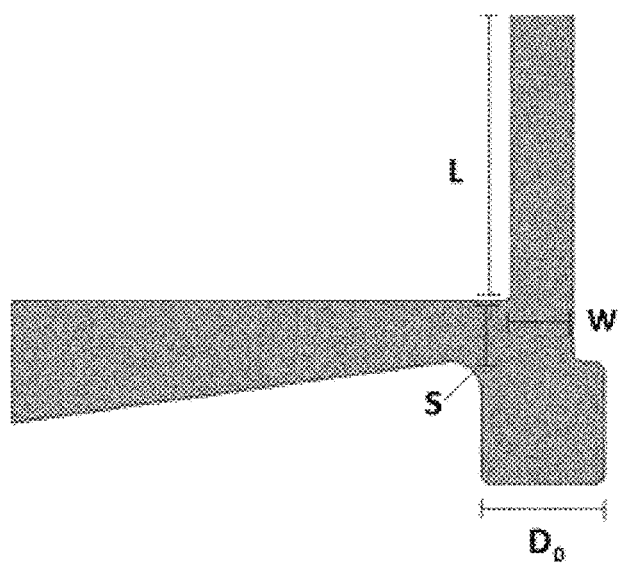
Figure 16A:
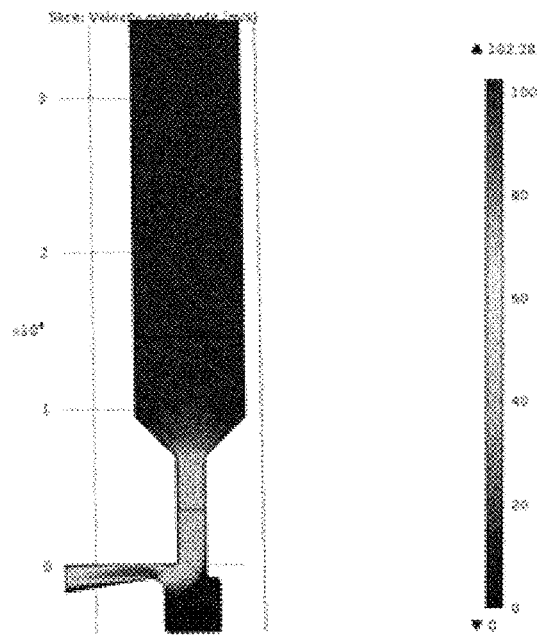
Figure 16B:
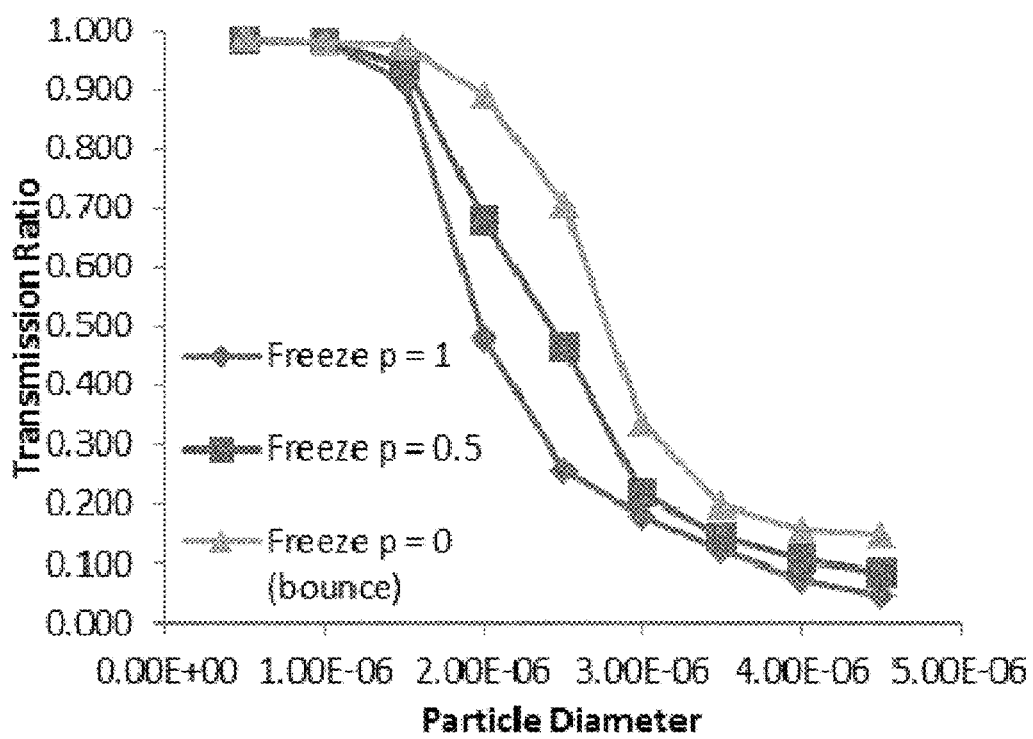

The acceleration inlet focuses the particles inertially, increasing the sharpness of the cut-off curve as shown in FIG. 14. The acceleration inlet is included in all the simulations to better represent an optimized impactor.

Transmission Ratio

Figure 3:
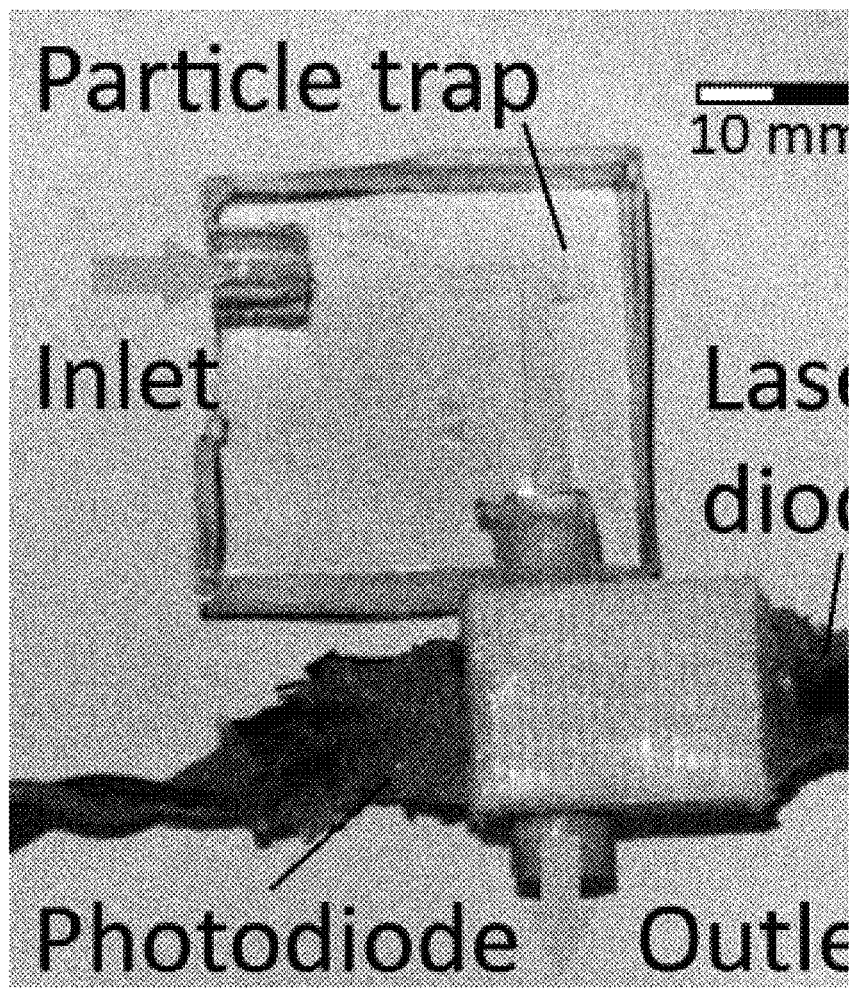
FIG. 3 illustrates an integrated PM detector according to an example embodiment.

The difference in velocity of flow streamlines along the width and height of the channel must be accounted for in order to obtain a better estimation of the particle transmission ratio. The particle cut-off characteristics of the impactor are simulated using Comsol™ Multiphysics (v4.3b). The flow field within the impactor was first solved using the Laminar Flow module by setting the 0.5 LPM flow rate inlet boundary condition. Particles were released uniformly at the inlet with the Particle Tracing module and the number of particles transmitted to the outlet was computed for particle sizes from 0.5 to 4 μm. The geometry of the particle trap impactor such as the impactor width $W_i$ and nozzle to impactor distance S were tuned iteratively as a ratio of the nozzle width to optimize the shape of the impactor cut-off curve. The wall characteristics were also varied to test the cut-off curve's sensitivity to wall conditions.

In general, the functionality of the impactor is somewhat insensitive to the geometries of the impactor. Changing the shapes has a minor effect on the slope of the cut-off curve and only shifts the cut-off curve and the 50% cut-off particle diameter. As long as the flow rate is within practical ranges, the 50% cut-off diameter and the cut-off curve can be shifted by changing the flow rate. Having an acceleration inlet in all the simulations likely reduced the device performance sensitivity to the geometry as most of the particles are focused towards the center of the channel. However, while the cut-off curves are similar, some designs are more dependent on the wall conditions. Small features should be avoided (S=0.5, Wi=1 etc.) to minimize interaction with the wall. The impactor width is also limited by the flow rate. If the impactor width is larger, a higher flow rate is required to achieve same 50% cut-off diameter.

Simulation Parameters Characterization

The simulations were initially conducted in 2D to minimize computation time. However, some discrepancies were found in the flow profile and the transmission curve when the 2D simulations were validated in 3D. The viscosity of the fluid appears to be lower in 2D, likely caused by the lack of viscous effects along the height of the channel. As shown in FIG. 22, all the flow streamlines are compressed towards one side of the channel in the 2D simulation which is physically unfeasible. 2D simulation also does not account for the slower particles released near the top and bottom wall, resulting in a sharper cut-off curve as shown in FIG. 23. All the simulations to design the impactor geometry were done 3D as a result.

| | 3D Model Wi = 2 | | | | | | | | |
|---|---|---|---|---|---|---|---|---|---|
| | S = 0.5 | | | S = 1 | | | S = 1.5 | | |
| | Freeze | p = 0.5 | Bounce | Freeze | p = 0.5 | Bounce | Freeze | p = 0.5 | Bounce |
| d50: | 1.98 | 2.42 | 2.78 | 2.39 | 2.75 | 3.05 | 2.48 | 2.77 | 3.08 |
| Δ d50 | | 0.8 | | | 0.66 | | | 0.6 | |
| Slope: | −1.80 | −1.66 | −2.66 | −1.79 | −1.73 | −2.39 | −1.81 | −1.59 | −2.27 |
| Δ Slope | | 1 | | | 0.66 | | | 0.68 | |

| | 3D Model S = 1 | | | | | | | | |
|---|---|---|---|---|---|---|---|---|---|
| | Wi = 1 | | | Wi = 2 | | | Wi = 3 | | |
| | Freeze | p = 0.5 | Bounce | Freeze | p = 0.5 | Bounce | Freeze | p = 0.5 | Bounce |
| d50 | 2.02 | 2.44 | 2.94 | 2.39 | 2.75 | 3.05 | 2.08 | 2.28 | 2.47 |
| Δ d50 | | 0.92 | | | 0.66 | | | 0.39 | |
| Slope | −1.08 | −0.84 | −1.33 | −1.79 | −1.73 | −2.39 | −1.19 | −1.00 | −1.33 |
| Δ Slope | | 0.49 | | | 0.66 | | | 0.33 | |

The normalized slope value represents the slope of the cutoff curve between 30% to 70% transmission. A higher absolute value of the slope represents a more effective impactor with a sharper cutoff. When the impactor width is varied, the slope is sharpest with impactor width 2 times the nozzle width. However, varying the outlet width does not have a significant effect on the slope. The slope is only sensitive to wall conditions when the outlet is small (S=0.5 case) where particles are more likely to collide with side walls. Since the 30% and 70% transmission value are extrapolated, minor variation in the slope could be caused by random error in the calculation.

The 50% cut-off diameter is extrapolated from the transmission curve. The cut-off diameter is more sensitive to wall conditions for smaller feature sizes as particles are allowed to interact with the wall (Impactor width=1, Outlet width=1).

The simulations were repeated for different particle release parameters to test the sensitivity of the simulation results. The three available release options are uniform grid, mesh and density. Different particle numbers were used whenever possible. When the particles are released with a uniform grid, the results for large particles are very sensitive to the particle numbers as shown in FIG. 24. This is caused by more particles on slower streamlines when uniform grid is used. As the particle number increases, the result converges. The mesh grid also differs from the uniform grid option. The density option appears to be the best. Even with a particle number of 500, the result converges with the uniform grid with 2000 particles. The density option was used for all the simulations.

Prototype Fabrication
Particle Trap Impactor The prototype particle trap impactor was fabricated with polydimethylsiloxane (PDMS) using a molding process. The molding process generally followed the description provided in reference [5]. A 200 µm thick layer of negative photoresist polymer SU-8 (2075, Microchem) was spin-coated and patterned with photolithography on a silicon wafer to form the mold for the microchannel. The molded PDM (Sylgard 184, Dow Corning Company) was bonded to a flat PDMS piece using oxygen plasma. The inlet and outlet ports of the microfluidic device were created by making a 4 mm circular cut with a hole puncher from the side wall of the PDMS device and a cut from the bottom of the device to release the core from the hole. The ports are in line with the microchannel to reduce particle loss caused by vertical connection. A third thin piece of PDMS was oxygen plasma-bonded to the bottom of the device to seal the cut. The side inlet and outlet ports provide a direct interface with the detector and other tubing adapters in the experiment setup as shown in FIG. 3.

Detector

Figure 4:
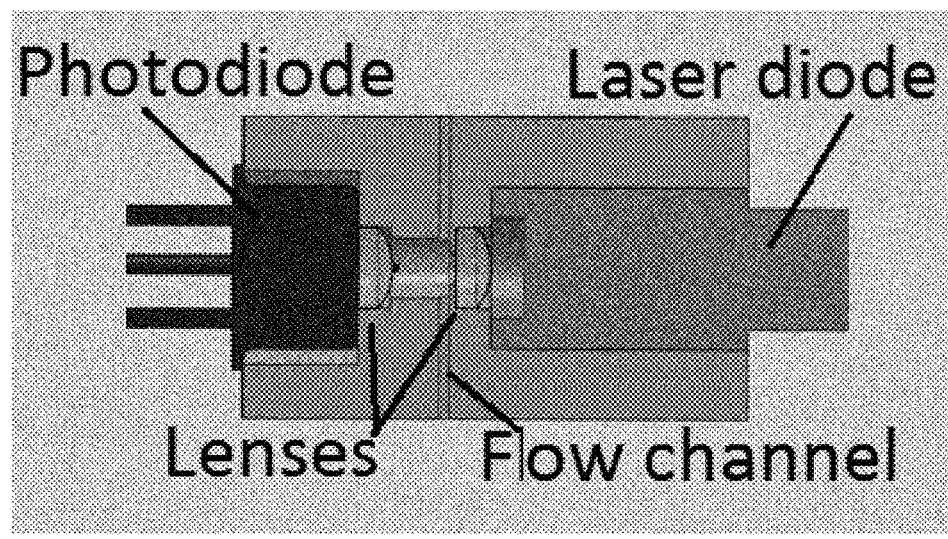
FIG. 4 illustrates an assembly model of a particle detection system according to an example embodiment of the present invention.

All the optical components were mounted into the 3D printed enclosure of the optical particle detector. A 0.5 by 1 mm rectangular flow channel directs the sample air stream to the detection system (FIG. 4). A solid model of the enclosure was constructed in Solidworks™ (v 2013) based on calculated design dimensions and the enclosure was produced using a personal 3D printer (24, Objet). Two 4 mm diameter plan convex lenses (47-861, Edmund Optics) were press fitted into the printed slots on both sides of the flow channel to focus the laser light onto the particle stream and collect the scattered light from particles into the detector. The light trap on the collection lens is formed by creating a mask from aluminum foil with a 0.5 mm hole on the lens and applying multiple layers of black acrylic spray paint (1602, Krylon).

A red 650 nm laser diode (AH-650-5-801, Aixiz) and a photodiode (SD100-14-21-021, Advanced Photonix) were fitted on opposite sides of the enclosure to complete the detection system. A two part gel epoxy (Lepage) was used to fix the photodetector to the enclosure. Silicone sealant (SE1122 3TG, GE) were also applied to both the laser diode and the photodiode to prevent flow leakage. An assembly model of the system is shown in FIG. 4.

The current signal from the detector was amplified and converted to a voltage signal using a transimpedance amplifier circuit. A RC high pass filter was used to remove DC bias in the signal due to stray light. A USB DAQ (USB-204, Measurement Computing) was used to log the data at 500 kS/s. The saved data was processed with a threshold level detection script in Matlab™ (R2013b) to obtain the detector count.

Experimental Setup

Figure 5:
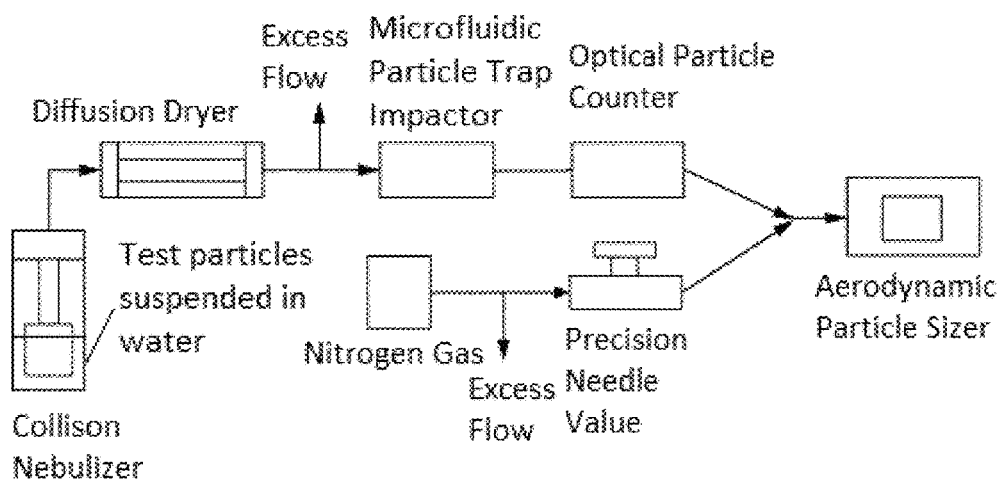
FIG. 5 illustrates an experimental setup that may be used to aerosolize polystyrene particles from a suspension for purposes of testing or calibrating a particle size selector.

Test particles were generated from suspensions of polystyrene microspheres using a 1-jet Collision nebulizer (CN241, BGI) followed by a diffusion drying column to remove moisture from the air stream. The aerosolized particles then passed through the microfluidic particle trap impactor and detector, and were then mixed with nitrogen gas to match the flow rate of TSI Aerodynamic Particle Sizer (APS) (3320, TSI). A precision needle value was used to control the flow resistance in the nitrogen gas line in order to maintain the 0.5 LPM flow rate through the separator device under test. The particles exiting the test device were counted by the APS. FIG. 5 shows the experimental setup for characterizing the sensor.

Experimental Results
Cut-Off Diameter of Particle Trap Impactor

Figure 6:
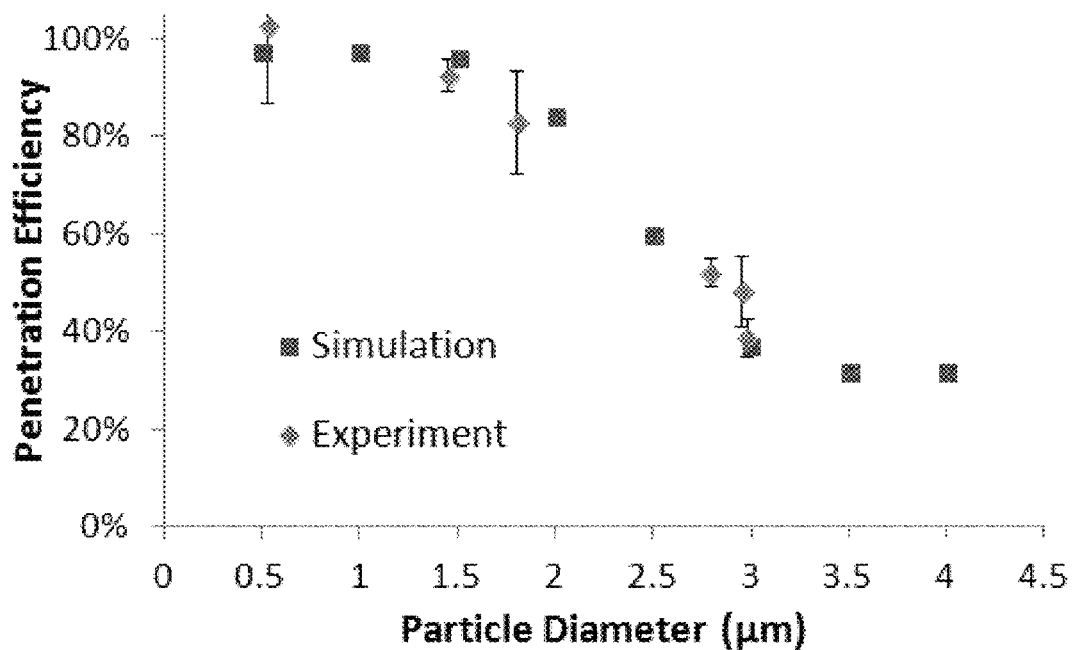

Particle sizes from 0.5 µm to 3 µm increments were used to characterize the performance of the particle trap impactor. The number of particles exiting the impactor was compared against the number of particles at the outlet of an equivalent straight microchannel to obtain the penetration efficiency of the impactor. FIG. 6 shows the experimental results of the percentage of particles passing through the impactor compared with the simulation results from Comsol™ Multiphysics. The aerodynamic particle diameters measured by the APS deviated from the diameters reported by the particle manufacturer. The experimental penetration efficiency curve using the APS-measured particle diameter values matched the simulation results with a 50% cutoff diameter around 2.5 µm. As expected, most of the smaller particles passed through the microfluidic device while a significant portion of the larger particles was captured. The penetration curve does not drop rapidly to zero for particle sizes above the 50% cut-off. This is thought to be due to larger particles travelling on the slower streamlines near the top and bottom wall of the microchannel where they experience a smaller centrifugal force as they travel around the corner at the particle trap as verified in the simulations.

Detector Counting Efficiency

Figure 7:
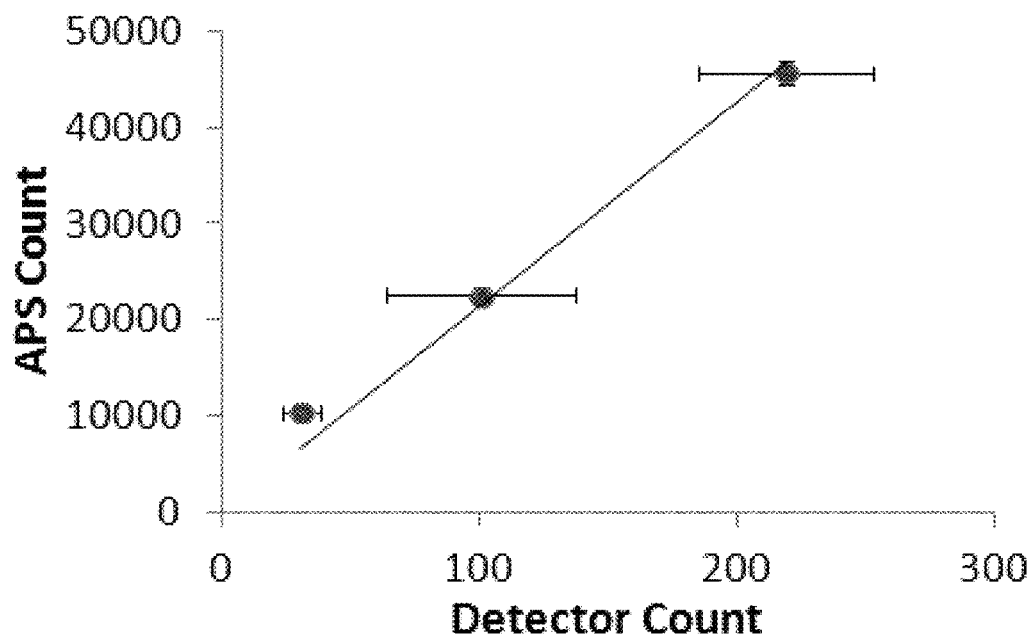

The detector was tested with 1.5 µm particles and the count was directly compared to the APS count. The detector count demonstrated good linear correlation with the APS count over 1 minute sampling intervals as shown in FIG. 7 as well as a reasonably high repeatability. The counting efficiency of the detector is around 0.5%, significantly lower than the APS. The lower optical power of the laser and the relatively low sensitivity of the photodiode used in the detector contribute to the low efficiency. Furthermore, flow expansion inside the chamber of the optical detector could allow particles to avoid the sensing region.

The prototype microchannel-based impactor design was shown to be effective to capture airborne particles larger than 2.5 µm. The measured penetration efficiency curve of the impactor agreed well with the simulation results. The separator was integrated with a low-cost optical detector. A linear correlation between the detector and a commercial particle detector was shown, demonstrating the potential of using microfluidic technology with integrated optics as a compact, wearable device for continuous PM 2.5 personal exposure monitoring.

The size of the particle trap limits the lifetime of the particle separator as it will eventually fill up with large particles unless purged of particles as described elsewhere herein.

Cascading (or "Series") Particle Size Selectors

The same impactor design with a smaller nozzle width can be incorporated downstream to size smaller particles. This was verified in simulation with a cascading particle trapping impactor model. The 2D impactor model with cut-off diameter designed to be 1 µm and 2.5 µm for 500 ml/min. However, flow velocity was too high and could not be solved. The final model has a 50% cut-off of 1.5 µm and 3 µm. The cut-off characteristics after the first stage of the cascading impactor is identical to the single impactor model as shown in FIG. 25. Due to the high number of elements, this could not be verified in 3D with the current computer setup.

REFERENCES

The following references are all hereby incorporated herein by reference for all purposes:

[1] U.S. Environmental Protection Agency, "National Ambient Air Quality Standards for Particulate Matter: Final Rule", *Federal Register*, vol. 78, no. 10, 2013.

[2] U.S. Environmental Protection Agency, "Quantitative Health Risk Assessment for Particulate Matter", 2010.

[3] J. S. Kang, K. S. Lee, K. H. Lee, H. J. Sung, and S. S. Kim, "Characterization of a Microscale Cascade Impactor", *Aerosol Sci. Technol.*, vol. 46, p. 966-972, 2012.

[4] D. Park, Y.-H. Kim, C. W. Park, J. Hwang, and Y.-J. Kim., "New bio-aerosol collector using a micromachined virtual impactor", *Journal of Aerosol Science, vol. 40*, issue 5, p. 415-422, 2009.

[5] A. Schaap, W. C. Chu, B. Stoeber, "Continuous size-separation of airborne particles in a microchannel for aerosol monitoring", *IEEE Sensors Journal*, vol. 11, issue 11, p. 2790-2797, 2011.

[6] I. Paprotny, F. Doering, P. A. Solomon, R. M. White, and L. A. Gundel, "Microfabricated air-microfluidic sensor for personal monitoring of airborne particulate matter: Design, fabrication, and experimental results", *Sensors and Actuators A: Physical*, 2013.

[7] H. H. Lim, D. Park, J. Y. Maeng, J. Hwang, and Y. J. Kim, "MEMS Based Integrated Particle Detection Chip for Real Time Environmental Monitoring", *Micro Electro Mechanical Systems*, 2006. MEMS 2006 Istanbul. 19th IEEE International Conference on, pp. 62, 65, 2006.

[8] E. Mehdizadeh, J. C. Wilson, A. Hajjam, A. Rahafrooz, and S. Pourkamali, "Aerosol impactor with embedded MEMS resonant mass balance for real-time particulate mass concentration monitoring", *Transducers & Eurosensors XXVII: The 17th International Conference on*, pp. 661-664, 2013.

[9] V. A. Marple and K. Willeke, "Impactor design", *Atmospheric Environment* (1976), vol. 10, no. 10, pp. 891-896, 1976.

[10] J. Gebhart, "Optical Direct-Reading Techniques: Light Intensity Systems", in *Aerosol Measurement: Principles, Techniques, and Application,* 2nd ed. New York: Wiley, 2001, pp. 419-450.

[11] P. Laven, "Simulation of rainbows, coronas, and glories by use of Mie theory", *Applied Optics*, vol. 42, issue 3, pp. 436-444, 2003.

Interpretation of Terms

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms;
the term "particulate" includes aerosol particulates.
The term 'impactor' is used as a short way to refer to impactor-type particle size selectors.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention which include components that perform control functions and/or calculation functions may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Where a component (e.g. a pump, particle counter, controller, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An apparatus for monitoring particulate matter, the apparatus defining a fluid flow passage having an inlet and an outlet, a particle size selector in the fluid-flow passage between the inlet and the outlet, the particle size selector comprising a curve section in the fluid flow passage wherein a direction of flow of fluid flowing in the fluid flow passage is changed and an impact surface extending transversely to the fluid flow passage on an outside of the curve section and an accelerating nozzle immediately upstream from the curve section wherein the width of the fluid flow passage is reduced in the accelerating nozzle;
   a particle counter located downstream from the particle size selector; and
   a pump connected to drive a flow of a fluid containing the particulate matter through the fluid flow passage.

2. The apparatus according to claim 1 comprising a cartridge defining a part of the fluid flow passage extending from a cartridge inlet to a cartridge outlet, wherein the cartridge has a planar configuration and the curve is in a plane of the cartridge.

3. The apparatus according to claim 2 wherein the fluid flow passage is flattened and has a width in the plane of the cartridge that is significantly greater than a height of the fluid flow passage perpendicular to the plane of the cartridge.

4. The apparatus according to claim 1 wherein in the accelerating nozzle the flow passage has a width in the range of 1400 μm to about 2000 μm.

5. The apparatus according to claim 4 wherein in the accelerating nozzle the flow passage has a height in the range of 150 μm to 500 μm.

6. The apparatus according to claim 1 wherein in the accelerating nozzle the flow passage has an aspect ratio of width to height in the range of 5:1 to 9:1.

7. The apparatus according to claim 1 wherein in the accelerating nozzle the flow passage has a width of 1700 μm±5% and a height of 250 μm±5%.

8. The apparatus according to claim 1 wherein a ratio of a length of the accelerating nozzle to the width of the accelerating nozzle is 3:1 or greater.

9. The apparatus according to claim 1 wherein the walls of the flow passage are tapered at angles in the range of 30 to 60 degrees immediately upstream from the acceleration nozzle.

10. The apparatus according to claim 1 wherein the width of the impact surface is at least 1¾ times the width of the accelerating nozzle.

11. The apparatus according to claim 1 wherein the impact surface comprises a surface extending parallel to a longitudinal axis of the accelerating nozzle.

12. The apparatus according to claim 11 wherein the line on which the impact surface lies is spaced apart from an edge of the accelerating nozzle closest to the outside of the curve by a distance greater than the width of the accelerating nozzle.

13. The apparatus according to any claim 1 wherein an output end of the accelerating nozzle is directed toward a chamber bounded on one side by the impact surface.

14. The apparatus according to claim 13 comprising a fluid port in the chamber, a fluid source connected to the fluid port and a valve operable to allow fluid from the fluid source to enter the chamber.

15. The apparatus according to claim 1 wherein, when the pump is operating, the particle size selector is operative to remove at least 50% of particles having sizes in excess of 3 μm from the fluid flowing through the particle size selector.

16. The apparatus according to claim 1 comprising a processor connected to receive an output from the particle counter and to process the output of the particle counter to yield a measure of mass concentration of particles counted by the particle counter in the fluid flowing in the fluid flow passage.

17. The apparatus according to claim 1 comprising a data logger comprising a processor and a data store, the data logger connected to receive an output of the particle counter and operative to record in the data store values indicative of the number of particles counted by the particle counter in different time periods.

18. The apparatus according to claim 1 wherein the particle size selector is a first of a plurality of particle size selectors connected in series in the fluid flow path and particle size cut-offs for the particle size selectors decrease sequentially in a downstream direction.

19. The apparatus according to claim 18 comprising a particle counter arranged to count particles in the fluid flow path between the first particle size selector and a second particle size selector downstream from the first particle size selector.

20. The apparatus according to claim 1 wherein the Reynolds number at the accelerating nozzle is in the range of 500 to 3000.

* * * * *